Figure 1B:
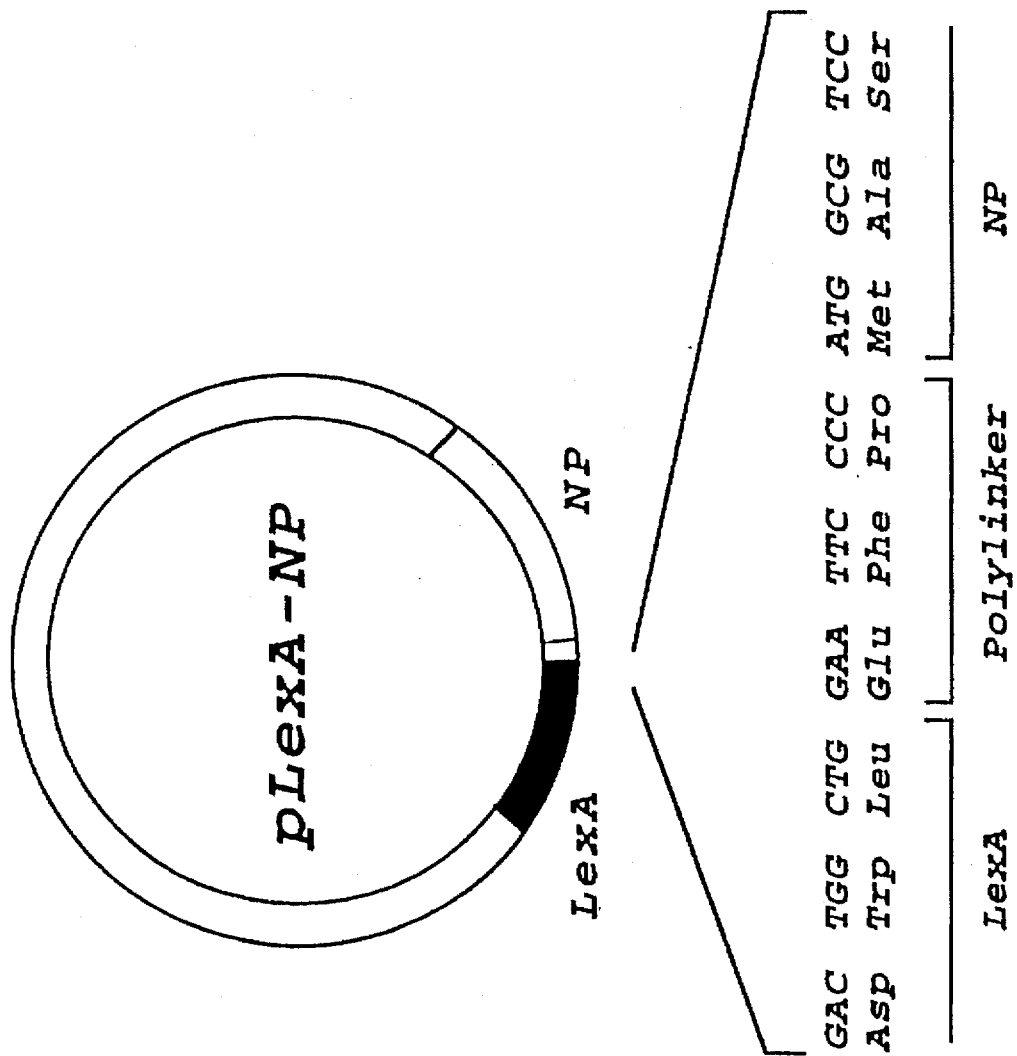

United States Patent [19]
Palese et al.

[11] Patent Number: 5,750,394
[45] Date of Patent: May 12, 1998

[54] IDENTIFICATION AND USE OF ANTIVIRAL COMPOUNDS THAT INHIBIT INTERACTION OF HOST CELL PROTEINS AND VIRAL PROTEINS REQUIRED FOR VIRAL REPLICATION

[75] Inventors: Peter Palese, Leonia, N.J.; Robert O'Neill, New York, N.Y.

[73] Assignee: The Mount Sinai Medical Center, New York, N.Y.

[21] Appl. No.: 246,583

[22] Filed: May 20, 1994

[51] Int. Cl.$^6$ .......................... C12N 1/21; C12N 15/63; C12N 5/10; C07H 21/04
[52] U.S. Cl. .......................... 435/252.3; 435/320.1; 435/325; 536/23.5
[58] Field of Search .......................... 435/320.1, 252.3, 435/325; 536/23.5

[56] References Cited

PUBLICATIONS

Scholtissek, et al., 1985, Virology 147: 287–294.
Bean, 1984, Virology 133: 438–442.
Buckler–White & Murphy, 1986, Virology 155: 345–355.
Gammelin, et al. 1989, Virology 170:71–80.
Scholtissek, et al. 1978, Virology 91: 79–85.
Huang, et al., 1990, J. Virol. 64: 5669–5673.
Beaton & Krug, 1986, Proc. Natl. Acad. Sci USA 83:6282–6286.
Shapiro & Krug, 1988, J. Virol. 62: 2285–2290.
Honda, et al., 1988, J. Biochem. 104: 1021–1026.
Barik & Banerjee, 1992, Proc. Natl. Acad. Sci. USA 89: 6570–6574.
Barik & Banerjee, 1992, J. Virol. 66: 1109–1118.
Lahiri & Thomas, 1986, Nucl. Acids Res. 14: 4077–4094.
Chelsky et al., 1989, "Sequence requirements for synthetic peptide–mediated translocation to the nucleus", Mol. Cell. Biol. 9:2487–2492.
Chien et al., 1991, "The two-hybrid system: A method to identify and clone genes for proteins that interact with a protein of interest", PNAS USA 88:9578–9582.
Cuomo et al., 1994, Mtg abstr. F015, Keystone Symp. on Recombination.
Dalton & Treisman, 1992, "Characterization of SAP-1, a protein recruited by serum response factor to the c-fos serum response element", Cell 68:597–612.
Durfee et al., 1993, "The retinoblastoma protein associates with the protein phosphatase type 1 catalytic subunit", Genes Dev. 7:555–569.
Enami et al., 1990, "Introduction of site-specific mutations into the genome of influenza virus", PNAS USA 87:3802–3805.
Gyuris et al., 1993, "Cdi1, a human G1 and S phase protein phosphatase that associates with Cdk2", Cell 75:791–803.
Hall et al., 1984, "Targeting of E. coli β–Galactosidase to the nucleus in yeast", Cell 36:1057–1065.

Jackson et al., 1982, "Influenza virus RNA is synthesized at fixed sites in the nucleus", Nature 296:366–368.
McCrea et al., 1991, "A homolog of the armadillo protein in Drosophila (Plakoglobin) associated with E–Cadherin", Science 254:1359–1361.
Parvin et al., 1989, "Promoter analysis of influenza virus RNA polymerase", J. Virol. 63:5142–5152.
Peifer et al., 1994, "A repeating amino acid motif shared by proteins with diverse cellular roles", Cell 76:789–791.
Riggleman et al., 1989, "Molecular analysis of the armadillo locus: Uniformly distributed transcripts and a protein with novel internal repeats are associated with a Drosophila segment polarity gene", Genes & Dev. 3:96–113.
Vojtek et al., 1993, "Mammalian Ras interacts directly with the Serine/Threonine kinase Raf", Cell 74:205–214.
Yano et al., 1992, "Cloning and characterization of SRP1, a suppressor of temperature-sensitive RNA polymerase 1 mutations, in Saccharomyces cerervisiae", Mol. Cell. Biol. 12:5640–5651.
Zervos et al., 1993, "Mxi1, a protein that specifically interacts with Max to bind Myc–Max recognition sites", Cell 72:222–232.
Baudin et al., 1994, "Structure of influenza virus RNP. 1. Influenza virus nucleoprotein melts secondary structure in panhandle RNA and exposes the bases to the solvent", EMBO J. 13:3158–3165.
Joklik et al. (eds.), 1992, "Antiviral chemotherapy, interferon, and vaccines", Zinsser Microbiology Appleton & Lange, Norwalk, Conn. Chap. 58, pp. 854–861.
Nakada et al., 1984, "Complete nucleotide sequence of the influenza C/California/78 virus nucleoprotein gene", Virus Res. 1:433–441.
Yano, R. et al. (1992) "Cloning and characterization of SRP1, a suppressor of temperature-sensitive RNA polymerase 1 mutations, in *Saccharomyces cerevisiae*" *Mol. Cell. Biol.* 12(12):5640–5651.

*Primary Examiner*—Robert A. Wax
*Assistant Examiner*—Kawai Lau
*Attorney, Agent, or Firm*—Pennie & Edmonds LLP

[57] ABSTRACT

The present invention relates to the identification of host cell proteins that interact with viral proteins required for virus replication, and high throughput assays to identify compounds that interfere with the specific interaction between the viral and host cell protein. Interfering compounds that inhibit viral replication can be used therapeutically to treat viral infection.

The invention is based, in part, on the discovery described herein of a novel interaction between the NP of influenza virus and a human host cell protein. The host cell protein, referred to herein as NPI-1, may be an accessory protein required for replication of influenza virus. Compounds that interfere with the binding of the host cell and viral proteins, and inhibit viral replication can be useful for treating viral infection in vivo.

11 Claims, 16 Drawing Sheets

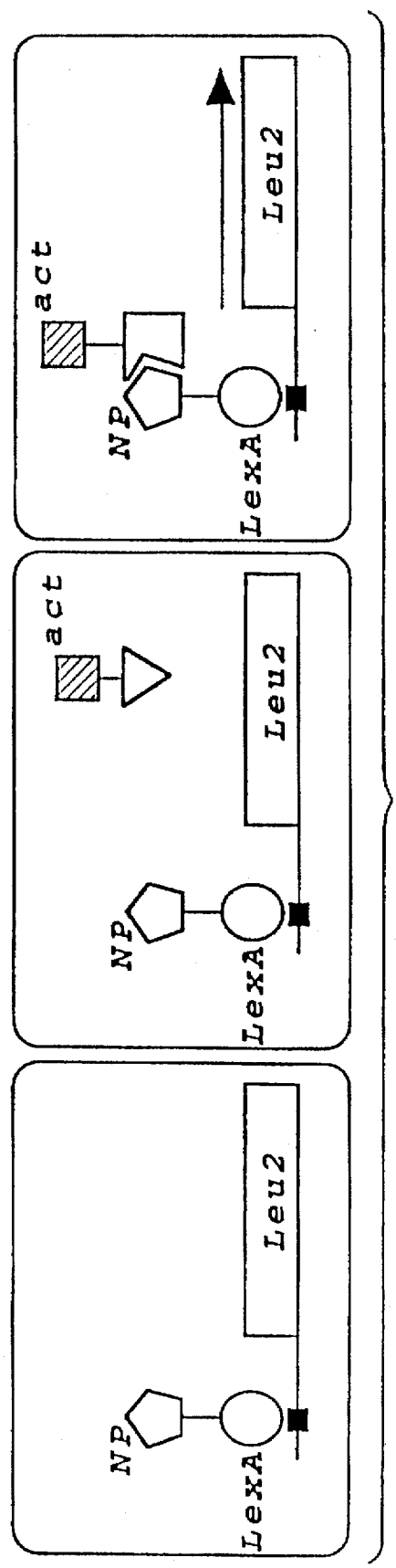
F I G. 1A

-40                                    -20                                   -1
                                                    CTAACTTCAGGCGTGGCACGGGATCGGTTGCCTTGAGCCTGAAAT
                                     20                                    40                                    60                                    80
ATGACCACCCCCAGGAAAGAGAACTTTCGCCTGAAAAGTTACAAGAACAAATCTCTGAATCCCGATGTGATGCGCAGGAG
 M  T  T  P  R  K  E  N  F  R  L  K  S  Y  K  N  K  S  L  N  P  D  V  M  R  R  R 100                                   120                                   140                                   160
GAGGAGCAGCTGTTCAAGAGAAGAAATGTTGTTACAGCAG
GAGGAGCAGCTGTTCAAGCGCAGTTACGAAAGAGAAGAGCAGTTATTCAAGAGAAGAAATGTTGTTACAGCAG
 R  I  I  G  I  Q  I  R  K  L  K  R  E  E  Q  L  F  K  R  R  N  V  V  T  A 180                                   200                                   220                                   240
AAGAAGAAGATGCTTCTGAGATGGAGGCTTTCATGAGGCTCAGATTAGTAACATGGAGATGGCACCAGGT
   I  I  I  V  M  S  D  G  G  F  H  E  A  Q  I  S  N  M  E  M  A  P  G 260                                   280                                   300                                   320
GGTGTATCTTCTGACATGATGATTGAGATGATATTTCAAAAGCCCAGAGCAACAGCTTCAGCAACACAGAAATTCAG
 G  V  I  S  D  M  I  E  M  I  F  S  K  S  P  E  Q  Q  L  S  A  T  Q  K  F  R 340                                   360                                   380                                   400
AAGGTGCTTTCAAAAGACCTGACCCCTCCTATTGATGAAGTTATCAGCACACCAGGAGTAGTGGCCAGGTTTGTGGAGT
 K  V  L  S  K  I  P  D  D  P  P  I  D  E  V  I  S  T  P  G  V  V  A  R  F  V  E 420                                   440                                   460                                   480
TCCTCAAAGGAAAGAGAATTGTCACTGCAGTTTGAATCAGCTGGGTACTGACAAATATTGCTTCAGGAAATTCTCTT
 L  K  R  K  I  N  C  S  L  Q  F  E  S  A  W  V  L  T  N  I  A  S  G  N  S  L

FIG. 2A

CAGACCCGAATTGTCGATTCAGGCAAGAGCTGTGCCATCTTCATAGAGTTGCTCAGTCAGAGTCTGAAGATGTCCAGGA
Q  T  R  I  V  I  Q  A  R  A  V  P  I  F  I  E  L  L  S  S  E  S  E  D  V  Q  E

ACAGGCAGTCTGGGCTCTTGGCAACATTGCTGGAGATAGTACCATGTGCAGGGACTATGTCTTAGACTGCAATATCCTTC
Q  A  V  W  A  L  G  N  I  A  G  D  S  T  M  C  R  D  Y  V  L  D  C  N  I  L

CCCCTCTTTTGCAGTTATTTTCAAAGCAAAAATCGCCTGACCATGACCCGGAATGCAGTAGTGGGCTTTGTCTAATCTCTGT
P  P  L  L  Q  L  F  S  K  Q  N  R  I  I  M  I  R  N  A  V  V  W  A  L  S  N  L  C

AGAGGGAAAAGTCCACCTCCAGAATTTGCAAAGGTTTCTTCCATGGTCTGAATGTGCTTTCCTGGTTGCTGTTGTCAGTGA
R  G  K  S  P  P  P  E  F  A  K  V  S  P  C  I  N  V  L  S  W  L  L  F  V  S  D

CACTGATGTACTGGCTGATGCCTGCTGGGCCCTCTCATATCTATCAGATGGACCCAATGATAAAATTCAAGGGGTCATCG
T  D  V  L  A  D  A  C  W  A  L  S  Y  L  S  D  G  P  N  D  K  I  Q  A  V  I

ATGCGGAGTATGTAGAGACTGTTGAACTGCTGATGCATAATGATTATAAAGTGGTTTCCTGCTTTGCGAGCTGTGGGA
D  A  E  Y  V  E  T  V  E  L  L  M  H  N  D  Y  K  V  V  S  P  A  L  R  A  V  G

AACATTGTCACAGGGGATGATATTCAGACACAGGTAATTCTGAATTGCTCAGCTCTGCAGAGTTTATTGCATTGCTGAG
N  I  V  T  G  D  D  I  Q  T  Q  V  I  L  N  C  S  A  L  Q  S  L  I  H  L  L  S

FIG.2B

```
                    1060                1080                1100                1120
TAGCCCAAAGGAATCTATCAAAAAGGAAGCATGTTGGACGATATCTAATATTACAGCTGGAAATAGGGCACAGATCCAGA
 S  P  K  E  S  I  K  K  E  A  C  W  T  I  S  N  I  T  A  G  N  R  A  Q  I  Q 1140                1160                1180                1200
CTGTGATAGATGCCAACATTTTCCCAGCCCTCATTAGTATTTTACAAACTGCTGAATTTCGGACAAGAAAAGAAGCAGCT
 I  V  I  D  A  N  I  F  P  A  L  I  S  I  L  Q  T  A  E  F  R  T  R  K  E  A  A 1220                1240                1260                1280
TGGGCCCATCACAAATGCAACTTCTGGAGGATCAGTGAACAGATCAAGTACCTAGTAGAACTGGGTTGTATCAAGCCGCT
 W  A  I  I  N  A  T  S  G  G  S  A  E  Q  I  K  Y  L  V  E  L  G  C  I  K  P  L 1300                1320                1340                1360
CTGTGATATTGTCATGGACTCTAAGATTGTACAGGTTGCCCTAAATGGCTTGGAAAATATCCTGAGGCTTGGAG
 C  D  I  I  V  M  D  S  K  I  V  Q  V  A  L  N  G  L  E  N  I  L  R  L  G 1380                1400                1420                1440
AACCAGGAACGCCAAAAGGCACTGGAATCAATCCCTACTGTGCTTTGATTGAAGAAGCTTATGGTCTGGATAAAATT
 Q  I  A  K  R  N  G  T  G  I  N  P  Y  C  A  L  I  E  E  A  Y  G  I  D  K  I 1460                1480                1500                1520
GAGTTCTTACTGAGTCATGAAAACCAGGAGATCTACCAAAAGGCCTTTGATCTTATTGAGCATTACTTCGGGACCGAAGA
 E  F  L  L  S  H  E  N  Q  E  I  Y  Q  K  A  F  D  L  I  E  H  Y  F  G  T  E  D 1540                1560                1580                1600
TGAAGACAGCAGCATTGCACCCCAGGTTGACCTTACAGCAGCAGTACATCTTCCAACAGTGTGAGGCTCCTATGGAAGGT
 E  D  S  S  I  A  P  Q  V  D  L  T  A  A  V  H  L  P  T  V
```

FIG. 2C

```
                1620                1640                1660                1680
TTCCAGCTTTGAAGCAATACTCTGCTTTCACGTACCTGTGCTCAGACCAGGCTACCCAGTCGAGTCCTCTTGTGGAGCCC
                1700                1720                1740                1760
ACAGTCCTCATGGAGCTAACTTCTCAAATGTTTCCATAATACTGTTTGCGCTCATTTGCTTGCCTTGCGCACCTGCTCT
                1780                1800                1820                1840
CTTACACACATCTGGAAACCTCCGGCTCTCTGTGGTGGGATACCCTTCTAATAAAAGGGTAACCAGAACGGCCCACTCT
                1860                1880                1900                1920
CTTTTTACGGCTAGGCTTTGGAGATCCGCACTTACATTAGAGTTATGGGAATATACACATATTAATGTGGCTC
                1940                1960                1980                2000
CCTTTTTCTTGTGGGGGAATAAAAGAGGACTCCTCCATTCCCTTTAACATGGGGGAAAAAACTGACATTAAAAGATGA
                2020                2040                2060                2080
GACTAAAATCTTTATCTTGAATTTTACACAACTACTACGACAAGGGAGATGTTTAGACCTGTTGGTATACTTCAGAGTAC
                2100                2120                2140                2160
TTTTCATGAGTTCTTCCACAGTGAACCCTTGGATTACCTGGTGGCTTTTTCTAGCCAGATTGCATTAATCCTTACTGAGA
                2180                2200                2220                2240
TTGGATGGTTTTCTTTCCTCTATTGGGCCATTCTTCAGATATTAAAGTTAAACCATCCACTCCCTCACCTTCAGCCTTC
                2260                2280                2300                2320
AGTGAATGTGCTTTCTAGTTGTCAGGAATGCTGAAGAATTAACACTTTGACTCCTAAATGTGATACTGGTGGGTAAGAGC
```

FIG.2D

```
                    2340                       2360                     2380                          2400
AGGGCACATTTAATTTGTTCGGCTTTGCTTCTCTCTTTGGTCTGGGCACATTTAATTTGTTCGCTTTTGCTTCTCTTTTGGTC
                    2420                     2440                     2460                      2480
TTTTCGAATACTTAGTAATCGAAAAACCATATATCCTGTAATTTAATAAAAAAAAACTAAGGACGAAAAAACCCCTCCAATTTT
                  2500                      2520                     2540                       2560
CCCAAATGCAATCAGTGTAACTAGGGGCTGTGTTTCTGCATTAAAATAAATGTTTCAGGCTTTGTGGTCCTGATCAAGGT
                   2580                    2600                     2620                         2640
CCTCATTAAAAAATGGAGTTCACCCTAGGCTTTTCCCCTCTGTGACTGGCAGATAACACATACTTTTGAAAGTAACTTT
                  2660                   2680                      2700                       2720
GGGATTTTTTTCTTAGGTGCAGCTCGATTCTAATCTTTTCATGCTGCACACGATTCCTTAATCGATAGCATCCTTATC
                   2740                    2760                      2780                        2800
TGAAAGAAATAACCATCTTCTCAACATGACCTGCTTAACCCAAATAAGAACAGTGATCTTATAACCTCATTGTTTCCTAA
                 2820                     2840                      2860                       2880
TCTATTTTATTTCATCTCCTGCTAGTACTGTGCCGCTTCCCCCTCCCCCCACACAAAATAAAAACAGTATCTCGCTTCTG

GCTCATTTT
```

FIG.2E

```
                                                      1          12
NPI-1                                               MTTPGKENFRLK
                                                    |:    |||.
SRP1                                           MDNGTDSSTSKFVPEYRRT
         13                                                  58
NPI-1    SYKNKS-LNPDVMRRRREEEGLQLRKLKREEQLFKRRNVVTAEEETE
         ||||||  ||||  ||||||| |  ||||| ||||.|  |||| |.|.|.||
SRP1     NFKNKGRFSADELRRRRDTQQVELRKAKRDEALAKRRNFIPPTDGAD
         59                                            105
NPI-1    EEVMSDGGFHEAQISNMEMAPGGVITSDMIEMIFSKSPEQQLSATQK
         .|  .|||  ..|    ||..      |||.| |  |.. ||||||| |
SRP1     SDEEDESSVSADQQFYSQLQQ---ELPQMTQQLNSDDMQEQLSATVK
         106                                           150
NPI-1    FRKLLSKEPDPPIDE-VISTPGVVARFVEFLKR-KENCSLQFESAWV  |
         ||::||:|. ||||   |: :|||:|:|||::  ::   ||:|:||. |Repeat #1
SRP1     FRQILSREHRPPID--VVIQAGVVPRLVEFMRE-NQPEMLQLEAAWA  |
         151                                           192
NPI-1    LTNIASGNSLQTRI--VIQARAV-PIFIELLSS-ESEDVQE-QAVWA  |
         ||||||||.|  ||::  |::|||  |:||:||  : .| :|:|  ||:||  |Repeat #2
SRP1     LTNIASGTSAQTKV--VVDADAV-PLFIQLLYT-GSVEVKE-QAIWA  |
         193                                           235
NPI-1    LGNIAGDSTMCRDY--VLDCNIL-PPLLQLFSKQNRLTMTR-NAVWA  |
         |||:||||| .|||  ||||| :  |:|  ||:. |: :::.| .|.|: |Repeat #3
SRP1     LGNVAGDSTDYRDY--VLQCNAM-EPILGLFNS-NKPSLIR-TATWT  |
         236                                           277
NPI-1    LSNLCRGKSPPPEF--AKVSPCL-NVLSWLLFV-SDTDVLA-DACWA  |
         ||||||||.|.|::   : ||. |  .|: |::  ||:.|. ||||| |Repeat #4
SRP1     LSNLCRGKKPQPDW--SVVSQAL-PTLAKLIYS-MDTETLV-DACWA  |
         278                                           318
NPI-1    LSYLSDGPNDKIQA----VIDAEYVET-VELLMH-NDYKVVS-PALRA  |
         :|||||||:: |||    |||.  .||||  |  .|: |   :||||| |Repeat #5
SRP1     ISYLSDGPQEAIQA----VIDVRIPKRLVELLSH-ESTLVQT-PALRA  |
         319                                           360
NPI-1    VGNIVTGDDIQTQV----ILNCSALQSLLHLLSS-PKESIKK-EACWT  |
         |||||||:|||||     ::|  :.|.:|  ||| |||:||| ||||| |Repeat #6
SRP1     VGNIVTGNDLQTQV----VINAGVLPALRLLLSS-PKENIKK-EACWT  |
         361                                           402
NPI-1    ISNITAGNRAQIQT----VIDANIFPALISILQT-AEFRTRK-EAAWA  |
         |||||||||.|||:    ||||::|:|::|:|:. ||::|:|  || || |Repeat #7
SRP1     ISNITAGNTEQIQA----VIDANLIPPLVKLLEV-AEYKTKK-EACWA  |
```

FIG.3A

```
           403                                           445
NPI-1    ITNATSGG—SAEQIKYLVELGCIKPLCDLLTV-MDSKIVQ-VALNG  |
         |:||:|||   .::  |:|||. |||||||||||.:  |::|::  |:|:: |Repeat #8
SRP1     ISNASSGGLQRPDIIRYLVSQGCIKPLCDLLEI-ADNRIIE-VTLDA |
           446                                         490
NPI-1    LENILRLGEQEAKRNGTGINPYCALIEEAYGLDKIEFL-LSHENQEI
         ||||||:||.:  . .| .||   .:||.| |::|| |    :||:.|
SRP1     LENILKMGEADKEARGLNINENADFIEKAGGMEKI-FNCQQNENDKI 491                           527
NPI-1    YQKAFDLIEHYFGTEDE—DSSIAPQVDLTAAVHLPTV
         |:||:.:|| |||.|::  |.:::|| . .:    :|
SRP1     YEKAYKIIETYFGEEEDAVDETMAPQNAGNTFGFGSNVNQQFNFN
```

---

```
Repeat element Consensuses:
ARM:    L+NLS*+***N+*~~ALL**GGL-PALV+LL*S~*+E**L*~*AA*A
                A         ||   ]    I              I
                          VV   V    V              V NPI-1
& SRP1: LSNI*SG***QPQ~~*VVI*AGV*PPLV-LL*S~*~*E*K+E~ACWA
        I                    V A
```

FIG.3B

```
        10        20        30        40        50
AACGACCAAGAGGGTGTTCGACTGCTAGAGCCGAGCAGAACGTGCCTAAATCAAA 60        70        80        90       100       110
GGAACTTGTTTCTTCAAGCTCTTCTGGCAGTGATTCTGATAGCGAGGTTGACAAAAAAGT 120       130       140       150       160
TAAGTCAGGAAAAAGCAAGTTGCTCCAGAAAA--CTGT-AAGAACAAAGACAG
```

FIG.7

```
                                    10        20        30
                        TTCGGCAGCAGGGCGCCCGCCTCTTGGAG-GA 40        50        60        70        80
C-----GCCAAGGGAGCGGCGACGTGGCAGGGGGGCAAGAGTTAGCGACTAAGAGAGCGA 90       100       110
GTAGAGAGCAGAGTAGACTAACTATCTCGCGG
```

FIG.8

```
                    10        20        30        40
          AAGTCTAATAACCAGCGCTCGCTCTTAGACCATTAAGCAA 50        60        70
AAGGCAAAGAGAACAGTAACAGTAGGGTCGAAA
```

FIG. 9

```
                10        20        30        40
      CTGTAGAGAGGCAAGAAGTACATGGAGGAGAAGTACCAGCTCAAGA 50        60        70        80
AGGGAGCTGCTGGACGAGGCAGTGGAGTGGATCGTAGG
```

FIG. 10

```
              10        20        30        40
    CTACCCTGCCGCACAACCTGACAGAGGTCGCGCGCCCTCGGCGGTGCTC 50        60        70        80
ACCAGGCCTGCCTCTCCGCCGCACCTGCCACCGAG
```

FIG. 11

```
              10        20        30
     AAAGCTAAGAAGGATGACAGAGTGCTAAGA 40        50        60        70
GGAGAAGTTAGTACCTTGTCTAGTAGTATCTCGTTGCTAGGCAAAG
```

FIG.12

```
                   10        20        30
           GGAGACTGTGGCTTTGAGCATCCGTCAGAAGTC 40        50        60        70        80        90
CAGCATGAGTGCATCCCTCAGGCCATTCTGGGAAT-GATGT-CTGTGCCAGGCCAAGTCG 100       110       120       130       140       150
GGCATGGGAAAGACAGCAGTGTTTGTCTTGGCCACACTGCAACAGCTGGAGCCAGTTACT 160       170       180       190       200
-GGCAGGTGTCTGTGCTGGTGATGTGT-ACA-CTCGGAGTTGGCTTT-CAGATCAGCA--

210
-GATATGAG
```

FIG.13

```
            10        20        30        40        50
GCTAGGGAGTAACCGAGATTCGCTAAGAGGAGAAGTTAGCTACTTTGCTAGTAGTATCC 60        70
TTCTGCGCTAGAAAG
```

FIG.14

```
                                      10         20        30
                              CTGTTTGAACGTATGATTCTTGAGTTCTTG 40        50        60
AGATGGTTGTACTTTACCTTTGAAGGTAATCTACCTG
```

FIG.15

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 2935 base pairs
( B ) TYPE: nucleic acid
( C ) STRANDEDNESS: double
( D ) TOPOLOGY: unknown ( i i ) MOLECULE TYPE: cDNA ( i x ) FEATURE:
( A ) NAME/KEY: CDS
( B ) LOCATION: 47..1627

( x i ) SEQUENCE DESCRIPTION: SEQ ID NO:1:

```
CTAACTTCAG CGGTGGCACC GGGATCGGTT GCCTTGAGCC TGAAAT ATG ACC ACC        55
                                                   Met Thr Thr
                                                    1

CCA GGA AAA GAG AAC TTT CGC CTG AAA AGT TAC AAG AAC AAA TCT CTG      103
Pro Gly Lys Glu Asn Phe Arg Leu Lys Ser Tyr Lys Asn Lys Ser Leu
    5                   10                  15

AAT CCC GAT GTG ATG CGC AGG AGG AGG GAG GAA GAA GGA CTG CAG TTA      151
Asn Pro Asp Val Met Arg Arg Arg Arg Glu Glu Glu Gly Leu Gln Leu
20                  25                  30                  35

CGA AAG CTG AAA AGA GAA GAG CAG TTA TTC AAG CGG AGA AAT GTT GTT      199
Arg Lys Leu Lys Arg Glu Glu Gln Leu Phe Lys Arg Arg Asn Val Val
                40                  45                  50

ACA GCA GAA GAA GAA ACA GAA GAA GAA GTT ATG TCA GAT GGA GGC TTT      247
Thr Ala Glu Glu Glu Thr Glu Glu Glu Val Met Ser Asp Gly Gly Phe
            55                  60                  65

CAT GAG GCT CAG ATT AGT AAC ATG GAG ATG GCA CCA GGT GGT GTC ATC      295
His Glu Ala Gln Ile Ser Asn Met Glu Met Ala Pro Gly Gly Val Ile
        70                  75                  80
```

-continued

| | | | | | | | | | | | | | | | | |
|---|---|---|---|---|---|---|---|---|---|---|---|---|---|---|---|---|
| ACT | TCT | GAC | ATG | ATT | GAG | ATG | ATA | TTT | TCC | AAA | AGC | CCA | GAG | CAA | CAG | 343 |
| Thr | Ser | Asp | Met | Ile | Glu | Met | Ile | Phe | Ser | Lys | Ser | Pro | Glu | Gln | Gln | |
| | 85 | | | | 90 | | | | | 95 | | | | | | |
| CTT | TCA | GCA | ACA | CAG | AAA | TTC | AGG | AAG | CTG | CTT | TCA | AAA | GAA | CCT | GAC | 391 |
| Leu | Ser | Ala | Thr | Gln | Lys | Phe | Arg | Lys | Leu | Leu | Ser | Lys | Glu | Pro | Asp | |
| 100 | | | | | 105 | | | | | 110 | | | | | 115 | |
| CCT | CCT | ATT | GAT | GAA | GTT | ATC | AGC | ACA | CCA | GGA | GTA | GTG | GCC | AGG | TTT | 439 |
| Pro | Pro | Ile | Asp | Glu | Val | Ile | Ser | Thr | Pro | Gly | Val | Val | Ala | Arg | Phe | |
| | | | | 120 | | | | | 125 | | | | | 130 | | |
| GTG | GAG | TTC | CTC | AAA | CGA | AAA | GAG | AAT | TGT | TCA | CTG | CAG | TTT | GAA | TCA | 487 |
| Val | Glu | Phe | Leu | Lys | Arg | Lys | Glu | Asn | Cys | Ser | Leu | Gln | Phe | Glu | Ser | |
| | | | 135 | | | | | 140 | | | | | 145 | | | |
| GCT | TGG | GTA | CTG | ACA | AAT | ATT | GCT | TCA | GGA | AAT | TCT | CTT | CAG | ACC | CGA | 535 |
| Ala | Trp | Val | Leu | Thr | Asn | Ile | Ala | Ser | Gly | Asn | Ser | Leu | Gln | Thr | Arg | |
| | | 150 | | | | | 155 | | | | | 160 | | | | |
| ATT | GTG | ATT | CAG | GCA | AGA | GCT | GTG | CCC | ATC | TTC | ATA | GAG | TTG | CTC | AGC | 583 |
| Ile | Val | Ile | Gln | Ala | Arg | Ala | Val | Pro | Ile | Phe | Ile | Glu | Leu | Leu | Ser | |
| | 165 | | | | | 170 | | | | | 175 | | | | | |
| TCA | GAG | TCT | GAA | GAT | GTC | CAG | GAA | CAG | GCA | GTC | TGG | GCT | CTT | GGC | AAC | 631 |
| Ser | Glu | Ser | Glu | Asp | Val | Gln | Glu | Gln | Ala | Val | Trp | Ala | Leu | Gly | Asn | |
| 180 | | | | | 185 | | | | | 190 | | | | | 195 | |
| ATT | GCT | GGA | GAT | AGT | ACC | ATG | TGC | AGG | GAC | TAT | GTC | TTA | GAC | TGC | AAT | 679 |
| Ile | Ala | Gly | Asp | Ser | Thr | Met | Cys | Arg | Asp | Tyr | Val | Leu | Asp | Cys | Asn | |
| | | | | 200 | | | | | 205 | | | | | 210 | | |
| ATC | CTT | CCC | CCT | CTT | TTG | CAG | TTA | TTT | TCA | AAG | CAA | AAC | CGC | CTG | ACC | 727 |
| Ile | Leu | Pro | Pro | Leu | Leu | Gln | Leu | Phe | Ser | Lys | Gln | Asn | Arg | Leu | Thr | |
| | | | 215 | | | | | 220 | | | | | 225 | | | |
| ATG | ACC | CGG | AAT | GCA | GTA | TGG | GCT | TTG | TCT | AAT | CTC | TGT | AGA | GGG | AAA | 775 |
| Met | Thr | Arg | Asn | Ala | Val | Trp | Ala | Leu | Ser | Asn | Leu | Cys | Arg | Gly | Lys | |
| | | 230 | | | | | 235 | | | | | 240 | | | | |
| AGT | CCA | CCT | CCA | GAA | TTT | GCA | AAG | GTT | TCT | CCA | TGT | CTG | AAT | GTG | CTT | 823 |
| Ser | Pro | Pro | Pro | Glu | Phe | Ala | Lys | Val | Ser | Pro | Cys | Leu | Asn | Val | Leu | |
| | 245 | | | | | 250 | | | | | 255 | | | | | |
| TCC | TGG | TTG | CTG | TTT | GTC | AGT | GAC | ACT | GAT | GTA | CTG | GCT | GAT | GCC | TGC | 871 |
| Ser | Trp | Leu | Leu | Phe | Val | Ser | Asp | Thr | Asp | Val | Leu | Ala | Asp | Ala | Cys | |
| 260 | | | | | 265 | | | | | 270 | | | | | 275 | |
| TGG | GCC | CTC | TCA | TAT | CTA | TCA | GAT | GGA | CCC | AAT | GAT | AAA | ATT | CAA | GCG | 919 |
| Trp | Ala | Leu | Ser | Tyr | Leu | Ser | Asp | Gly | Pro | Asn | Asp | Lys | Ile | Gln | Ala | |
| | | | | 280 | | | | | 285 | | | | | 290 | | |
| GTC | ATC | GAT | GCG | GAG | TAT | GTA | GAG | ACT | GTG | GAA | CTG | CTG | ATG | CAT | AAT | 967 |
| Val | Ile | Asp | Ala | Glu | Tyr | Val | Glu | Thr | Val | Glu | Leu | Leu | Met | His | Asn | |
| | | | 295 | | | | | 300 | | | | | 305 | | | |
| GAT | TAT | AAA | GTG | GTT | TCT | CCT | GCT | TTG | CGA | GCT | GTG | GGA | AAC | ATT | GTC | 1015 |
| Asp | Tyr | Lys | Val | Val | Ser | Pro | Ala | Leu | Arg | Ala | Val | Gly | Asn | Ile | Val | |
| | | 310 | | | | | 315 | | | | | 320 | | | | |
| ACA | GGG | GAT | GAT | ATT | CAG | ACA | CAG | GTA | ATT | CTG | AAT | TGC | TCA | GCT | CTG | 1063 |
| Thr | Gly | Asp | Asp | Ile | Gln | Thr | Gln | Val | Ile | Leu | Asn | Cys | Ser | Ala | Leu | |
| | 325 | | | | | 330 | | | | | 335 | | | | | |
| CAG | AGT | TTA | TTG | CAT | TTG | CTG | AGT | AGC | CCA | AAG | GAA | TCT | ATC | AAA | AAG | 1111 |
| Gln | Ser | Leu | Leu | His | Leu | Leu | Ser | Ser | Pro | Lys | Glu | Ser | Ile | Lys | Lys | |
| 340 | | | | | 345 | | | | | 350 | | | | | 355 | |
| GAA | GCA | TGT | TGG | ACG | ATA | TCT | AAT | ATT | ACA | GCT | GGA | AAT | AGG | GCA | CAG | 1159 |
| Glu | Ala | Cys | Trp | Thr | Ile | Ser | Asn | Ile | Thr | Ala | Gly | Asn | Arg | Ala | Gln | |
| | | | | 360 | | | | | 365 | | | | | 370 | | |
| ATC | CAG | ACT | GTG | ATA | GAT | GCC | AAC | ATT | TTC | CCA | GCC | CTC | ATT | AGT | ATT | 1207 |
| Ile | Gln | Thr | Val | Ile | Asp | Ala | Asn | Ile | Phe | Pro | Ala | Leu | Ile | Ser | Ile | |
| | | | 375 | | | | | 380 | | | | | 385 | | | |
| TTA | CAA | ACT | GCT | GAA | TTT | CGG | ACA | AGA | AAA | GAA | GCA | GCT | TGG | GCC | ATC | 1255 |
| Leu | Gln | Thr | Ala | Glu | Phe | Arg | Thr | Arg | Lys | Glu | Ala | Ala | Trp | Ala | Ile | |
| | | 390 | | | | | 395 | | | | | 400 | | | | |

| | | | | | | | | | | | | | | | | |
|---|---|---|---|---|---|---|---|---|---|---|---|---|---|---|---|---|
| ACA | AAT | GCA | ACT | TCT | GGA | GGA | TCA | GCT | GAA | CAG | ATC | AAG | TAC | CTA | GTA | 1303 |
| Thr | Asn | Ala | Thr | Ser | Gly | Gly | Ser | Ala | Glu | Gln | Ile | Lys | Tyr | Leu | Val | |
| | | 405 | | | | 410 | | | | | 415 | | | | | |
| GAA | CTG | GGT | TGT | ATC | AAG | CCG | CTC | TGT | GAT | CTC | CTC | ACG | GTC | ATG | GAC | 1351 |
| Glu | Leu | Gly | Cys | Ile | Lys | Pro | Leu | Cys | Asp | Leu | Leu | Thr | Val | Met | Asp | |
| 420 | | | | | 425 | | | | | 430 | | | | | 435 | |
| TCT | AAG | ATT | GTA | CAG | GTT | GCC | CTA | AAT | GGC | TTG | GAA | AAT | ATC | CTG | AGG | 1399 |
| Ser | Lys | Ile | Val | Gln | Val | Ala | Leu | Asn | Gly | Leu | Glu | Asn | Ile | Leu | Arg | |
| | | | | 440 | | | | | 445 | | | | | 450 | | |
| CTT | GGA | GAA | CAG | GAA | GCC | AAA | AGG | AAC | GGC | ACT | GGC | ATT | AAC | CCT | TAC | 1447 |
| Leu | Gly | Glu | Gln | Glu | Ala | Lys | Arg | Asn | Gly | Thr | Gly | Ile | Asn | Pro | Tyr | |
| | | | 455 | | | | | 460 | | | | | 465 | | | |
| TGT | GCT | TTG | ATT | GAA | GAA | GCT | TAT | GGT | CTG | GAT | AAA | ATT | GAG | TTC | TTA | 1495 |
| Cys | Ala | Leu | Ile | Glu | Glu | Ala | Tyr | Gly | Leu | Asp | Lys | Ile | Glu | Phe | Leu | |
| | | 470 | | | | | 475 | | | | | 480 | | | | |
| CTG | AGT | CAT | GAA | AAC | CAG | GAG | ATC | TAC | CAA | AAG | GCC | TTT | GAT | CTT | ATT | 1543 |
| Leu | Ser | His | Glu | Asn | Gln | Glu | Ile | Tyr | Gln | Lys | Ala | Phe | Asp | Leu | Ile | |
| | | 485 | | | | | 490 | | | | | 495 | | | | |
| GAG | CAT | TAC | TTC | GGG | ACC | GAA | GAT | GAA | GAC | AGC | AGC | ATT | GCA | CCC | CAG | 1591 |
| Glu | His | Tyr | Phe | Gly | Thr | Glu | Asp | Glu | Asp | Ser | Ser | Ile | Ala | Pro | Gln | |
| 500 | | | | | 505 | | | | | 510 | | | | | 515 | |
| GTT | GAC | CTT | ACA | GCA | GCA | GTA | CAT | CTT | CCA | ACA | GTG | TGAGGCTCCT | | | | 1637 |
| Val | Asp | Leu | Thr | Ala | Ala | Val | His | Leu | Pro | Thr | Val | | | | | |
| | | | | 520 | | | | | 525 | | | | | | | |

```
ATGGAAGGTT TCCAGCTTTG AAGCAATACT CTGCTTTCAC GTACCTGTGC TCAGACCAGG      1697
CTACCCAGTC GAGTCCTCTT GTGGAGCCCA CAGTCCTCAT GGAGCTAACT TCTCAAATGT      1757
TTTCCATAAT ACTGTTTGCG CTCATTTGCT TGCCTTGCGC ACCTGCTCTC TTACACACAT      1817
CTGGAAAACC TCCGGCTCTC TGTGGTGGGA TACCCTTCTA ATAAAGGGT AACCAGAACG       1877
GCCCACTCTC TTTTACGGAA AAATCCCTAG GCTTGGAGA TCCGCACTTA CATTAGAGTT       1937
ATGGGAATAT ACACATATTA ATGTGGCTCC CTTTTCTTG TGGGGAATA AAAGAGGACT        1997
CCTCCTCATT CCCTTTAACA TGGGGGAAAA AACTGACATT AAAAGATGAG ACTAAATCTT      2057
TATCTTGAAT TTACACAAC TACTTACGAC AAGGGAGATG TTTAGACCTG TTGGTATACT       2117
TCAGAGTACT TTTCATGAGT TCTTCCACAG TGAACCCTTG GATTACCTGG TGGCTTTTTC      2177
TAGCCAGATT GCATTAATCC TTACTGAGAT TGGATGGTTT TCTTTCCTCT ATTGGCGCCA      2237
TTCTTCAGAT ATTAAAGTTA AACCATCCAC TCCCTCACCT TCAGCCTTCA GTGAATGTGC      2297
TTTCTAGTTG TCAGGAATGC TGAAGAATTA ACACTTTGAC TCCTAAATGT GATACTGGTG      2357
GGTAAGAGCA GGGCACATTT AATTTGTTCG CTTTTGCTTC TCTTTGGTCT GGGCACATTT      2417
AATTTGTTCG CTTTTGCTTC TCTTTGGTCT TTTCGAATAC TTAGTAATCG AAACCATAT       2477
CCTGTAATTT AATAAAAAAA ACTAAGGACG AAAAAACCCC TCCAATTTTC CCAAATGCAA      2537
TCAGTGTAAC TAGGGGCTGT GTTTCTGCAT TAAAATAAAT GTTTCAGGCT TTGTGGTCCT      2597
GATCAAGGTC CTCATTAAAA AATTGGAGTT CACCCTAGGC TTTTCCCCTC TGTGACTGGC      2657
AGATAACACA TACTTTTGAA AGTAACTTTG GGATTTTTT TCTTAGGTGC AGCTCGATTC       2717
TAATCTTTTC ATGCTGCACA CGATTCCTTT AATCGATAGC ATCCTTATCT GAAAGAAATA      2777
ACCATCTTCT CAACATGACC TGCTTAACCC AAATAAGAAC AGTGATCTTA TAACCTCATT      2837
GTTTCCTAAT CTATTTATT TCATCTCCTG CTAGTACTGT GCCGCTTCCC CCTCCCCCA        2897
CACAAAATAA AAACAGTATC TCGCTTCTGG CTCATTTT                              2935
```

( 2 ) INFORMATION FOR SEQ ID NO:2:

( i ) SEQUENCE CHARACTERISTICS:
    ( A ) LENGTH: 527 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met Thr Thr Pro Gly Lys Glu Asn Phe Arg Leu Lys Ser Tyr Lys Asn
 1               5                  10                  15

Lys Ser Leu Asn Pro Asp Val Met Arg Arg Arg Glu Glu Glu Gly
            20                  25                  30

Leu Gln Leu Arg Lys Leu Lys Arg Glu Glu Gln Leu Phe Lys Arg Arg
            35                  40                  45

Asn Val Val Thr Ala Glu Glu Thr Glu Glu Glu Val Met Ser Asp
        50                  55                  60

Gly Gly Phe His Glu Ala Gln Ile Ser Asn Met Glu Met Ala Pro Gly
 65                  70                  75                  80

Gly Val Ile Thr Ser Asp Met Ile Glu Met Ile Phe Ser Lys Ser Pro
                85                  90                  95

Glu Gln Gln Leu Ser Ala Thr Gln Lys Phe Arg Lys Leu Leu Ser Lys
            100                 105                 110

Glu Pro Asp Pro Pro Ile Asp Glu Val Ile Ser Thr Pro Gly Val Val
            115                 120                 125

Ala Arg Phe Val Glu Phe Leu Lys Arg Lys Glu Asn Cys Ser Leu Gln
        130                 135                 140

Phe Glu Ser Ala Trp Val Leu Thr Asn Ile Ala Ser Gly Asn Ser Leu
145                 150                 155                 160

Gln Thr Arg Ile Val Ile Gln Ala Arg Ala Val Pro Ile Phe Ile Glu
                165                 170                 175

Leu Leu Ser Ser Glu Ser Glu Asp Val Gln Glu Gln Ala Val Trp Ala
            180                 185                 190

Leu Gly Asn Ile Ala Gly Asp Ser Thr Met Cys Arg Asp Tyr Val Leu
            195                 200                 205

Asp Cys Asn Ile Leu Pro Pro Leu Leu Gln Leu Phe Ser Lys Gln Asn
    210                 215                 220

Arg Leu Thr Met Thr Arg Asn Ala Val Trp Ala Leu Ser Asn Leu Cys
225                 230                 235                 240

Arg Gly Lys Ser Pro Pro Pro Glu Phe Ala Lys Val Ser Pro Cys Leu
                245                 250                 255

Asn Val Leu Ser Trp Leu Leu Phe Val Ser Asp Thr Asp Val Leu Ala
            260                 265                 270

Asp Ala Cys Trp Ala Leu Ser Tyr Leu Ser Asp Gly Pro Asn Asp Lys
            275                 280                 285

Ile Gln Ala Val Ile Asp Ala Glu Tyr Val Glu Thr Val Glu Leu Leu
    290                 295                 300

Met His Asn Asp Tyr Lys Val Val Ser Pro Ala Leu Arg Ala Val Gly
305                 310                 315                 320

Asn Ile Val Thr Gly Asp Asp Ile Gln Thr Gln Val Ile Leu Asn Cys
                325                 330                 335

Ser Ala Leu Gln Ser Leu Leu His Leu Leu Ser Ser Pro Lys Glu Ser
            340                 345                 350

Ile Lys Lys Glu Ala Cys Trp Thr Ile Ser Asn Ile Thr Ala Gly Asn
        355                 360                 365

Arg Ala Gln Ile Gln Thr Val Ile Asp Ala Asn Ile Phe Pro Ala Leu
    370                 375                 380
```

```
Ile  Ser  Ile  Leu  Gln  Thr  Ala  Glu  Phe  Arg  Thr  Arg  Lys  Glu  Ala  Ala
385                      390                     395                      400

Trp  Ala  Ile  Thr  Asn  Ala  Thr  Ser  Gly  Gly  Ser  Ala  Glu  Gln  Ile  Lys
                    405                     410                      415

Tyr  Leu  Val  Glu  Leu  Gly  Cys  Ile  Lys  Pro  Leu  Cys  Asp  Leu  Leu  Thr
               420                     425                      430

Val  Met  Asp  Ser  Lys  Ile  Val  Gln  Val  Ala  Leu  Asn  Gly  Leu  Glu  Asn
          435                     440                      445

Ile  Leu  Arg  Leu  Gly  Glu  Gln  Glu  Ala  Lys  Arg  Asn  Gly  Thr  Gly  Ile
     450                     455                     460

Asn  Pro  Tyr  Cys  Ala  Leu  Ile  Glu  Glu  Ala  Tyr  Gly  Leu  Asp  Lys  Ile
465                      470                     475                      480

Glu  Phe  Leu  Leu  Ser  His  Glu  Asn  Gln  Glu  Ile  Tyr  Gln  Lys  Ala  Phe
                    485                     490                      495

Asp  Leu  Ile  Glu  His  Tyr  Phe  Gly  Thr  Glu  Asp  Glu  Asp  Ser  Ser  Ile
               500                     505                      510

Ala  Pro  Gln  Val  Asp  Leu  Thr  Ala  Ala  Val  His  Leu  Pro  Thr  Val
               515                     520                      525
```

( 2 ) INFORMATION FOR SEQ ID NO:3:

( i ) SEQUENCE CHARACTERISTICS:
        ( A ) LENGTH: 542 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:3:

```
Met  Asp  Asn  Gly  Thr  Asp  Ser  Ser  Thr  Ser  Lys  Phe  Val  Pro  Glu  Tyr
1                   5                   10                      15

Arg  Arg  Thr  Asn  Phe  Lys  Asn  Lys  Gly  Arg  Phe  Ser  Ala  Asp  Glu  Leu
               20                      25                      30

Arg  Arg  Arg  Arg  Asp  Thr  Gln  Gln  Val  Glu  Leu  Arg  Lys  Ala  Lys  Arg
          35                      40                      45

Asp  Glu  Ala  Leu  Ala  Lys  Arg  Arg  Asn  Phe  Ile  Pro  Pro  Thr  Asp  Gly
     50                      55                      60

Ala  Asp  Ser  Asp  Glu  Glu  Asp  Glu  Ser  Ser  Val  Ser  Ala  Asp  Gln  Gln
65                      70                      75                      80

Phe  Tyr  Ser  Gln  Leu  Gln  Gln  Glu  Leu  Pro  Gln  Met  Thr  Gln  Gln  Leu
                    85                      90                      95

Asn  Ser  Asp  Asp  Met  Gln  Glu  Gln  Leu  Ser  Ala  Thr  Val  Lys  Phe  Arg
               100                     105                     110

Gln  Ile  Leu  Ser  Arg  Glu  His  Arg  Pro  Pro  Ile  Asp  Val  Val  Ile  Gln
          115                     120                     125

Ala  Gly  Val  Val  Pro  Arg  Leu  Val  Glu  Phe  Met  Arg  Glu  Asn  Gln  Pro
     130                     135                     140

Glu  Met  Leu  Gln  Leu  Glu  Ala  Ala  Trp  Ala  Leu  Thr  Asn  Ile  Ala  Ser
145                     150                     155                     160

Gly  Thr  Ser  Ala  Gln  Thr  Lys  Val  Val  Asp  Ala  Asp  Ala  Val  Pro
                    165                     170                     175

Leu  Phe  Ile  Gln  Leu  Leu  Tyr  Thr  Gly  Ser  Val  Glu  Val  Lys  Glu  Gln
               180                     185                     190

Ala  Ile  Trp  Ala  Leu  Gly  Asn  Val  Ala  Gly  Asp  Ser  Thr  Asp  Tyr  Arg
          195                     200                     205
```

|     |     |     |     |     |     |     |     |     |     |     |     |     |     |     |
| --- | --- | --- | --- | --- | --- | --- | --- | --- | --- | --- | --- | --- | --- | --- |
| Asp | Tyr 210 | Val | Leu | Gln | Cys 215 | Asn | Ala | Met | Glu | Pro 220 | Ile | Leu | Gly | Leu | Phe |
| Asn 225 | Ser | Asn | Lys | Pro | Ser 230 | Leu | Ile | Arg | Thr | Ala 235 | Thr | Trp | Thr | Leu | Ser 240 |
| Asn | Leu | Cys | Arg | Gly 245 | Lys | Lys | Pro | Gln | Pro 250 | Asp | Trp | Ser | Val | Val 255 | Ser |
| Gln | Ala | Leu | Pro 260 | Thr | Leu | Ala | Lys | Leu 265 | Ile | Tyr | Ser | Met | Asp 270 | Thr | Glu |
| Thr | Leu | Val 275 | Asp | Ala | Cys | Trp | Ala 280 | Ile | Ser | Tyr | Leu | Ser 285 | Asp | Gly | Pro |
| Gln | Glu 290 | Ala | Ile | Gln | Ala | Val 295 | Ile | Asp | Val | Arg | Ile 300 | Pro | Lys | Arg | Leu |
| Val 305 | Glu | Leu | Leu | Ser | His 310 | Glu | Ser | Thr | Leu | Val 315 | Gln | Thr | Pro | Ala | Leu 320 |
| Arg | Ala | Val | Gly | Asn 325 | Ile | Val | Thr | Gly | Asn 330 | Asp | Leu | Gln | Thr | Gln 335 | Val |
| Val | Ile | Asn | Ala 340 | Gly | Val | Leu | Pro | Ala 345 | Leu | Arg | Leu | Leu | Leu 350 | Ser | Ser |
| Pro | Lys | Glu 355 | Asn | Ile | Lys | Lys | Glu 360 | Ala | Cys | Trp | Thr | Ile 365 | Ser | Asn | Ile |
| Thr | Ala 370 | Gly | Asn | Thr | Glu | Gln 375 | Ile | Gln | Ala | Val | Ile 380 | Asp | Ala | Asn | Leu |
| Ile 385 | Pro | Pro | Leu | Val | Lys 390 | Leu | Leu | Glu | Val | Ala 395 | Glu | Tyr | Lys | Thr | Lys 400 |
| Lys | Glu | Ala | Cys | Trp 405 | Ala | Ile | Ser | Asn | Ala 410 | Ser | Ser | Gly | Gly | Leu 415 | Gln |
| Arg | Pro | Asp | Ile 420 | Ile | Arg | Tyr | Leu | Val 425 | Ser | Gln | Gly | Cys | Ile 430 | Lys | Pro |
| Leu | Cys | Asp 435 | Leu | Leu | Glu | Ile | Ala 440 | Asp | Asn | Arg | Ile | Ile 445 | Glu | Val | Thr |
| Leu | Asp 450 | Ala | Leu | Glu | Asn | Ile 455 | Leu | Lys | Met | Gly | Glu 460 | Ala | Asp | Lys | Glu |
| Ala 465 | Arg | Gly | Leu | Asn | Ile 470 | Asn | Glu | Asn | Ala | Asp 475 | Phe | Ile | Glu | Lys | Ala 480 |
| Gly | Gly | Met | Glu | Lys 485 | Ile | Phe | Asn | Cys | Gln 490 | Gln | Asn | Glu | Asn | Asp 495 | Lys |
| Ile | Tyr | Glu | Lys 500 | Ala | Tyr | Lys | Ile | Ile 505 | Glu | Thr | Tyr | Phe | Gly 510 | Glu | Glu |
| Glu | Asp | Ala 515 | Val | Asp | Glu | Thr | Met 520 | Ala | Pro | Gln | Asn | Ala 525 | Gly | Asn | Thr |
| Phe | Gly 530 | Phe | Gly | Ser | Asn | Val 535 | Asn | Gln | Gln | Phe | Asn 540 | Phe | Asn |     |     |

( 2 ) INFORMATION FOR SEQ ID NO:4:

( i ) SEQUENCE CHARACTERISTICS:
        ( A ) LENGTH: 165 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:4:

```
AACGACCAAG AGGGTGTTCG ACTGCTAGAG CCGAGCAGAA CGTGCCTAAA TCAAAGGAAC    60
TTGTTTCTTC AAGCTCTTCT GGCAGTGATT CTGATAGCGA GGTTGACAAA AAAGTTAAGT   120
```

CAGGAAAAAG CAAGTTGCTC CAGAAAACTG TAAGAACAAA GACAG					165

( 2 ) INFORMATION FOR SEQ ID NO:5:

( i ) SEQUENCE CHARACTERISTICS:
        ( A ) LENGTH: 118 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:5:

TTCGGCAGCA GGGCGCCCGC CTCTTGGAGG ACGCCAAGGG AGCGGCGACG TGGCAGGGGG					60

GCAAGAGTTA GCGACTAAGA GAGCGAGTAG AGAGCAGAGT AGACTAACTA TCTCGCGG					118

( 2 ) INFORMATION FOR SEQ ID NO:6:

( i ) SEQUENCE CHARACTERISTICS:
        ( A ) LENGTH: 73 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:6:

AAGTCTAATA ACCAGCGCTC GCTCTTAGAC CATTAAGCAA AAGGCAAAGA GAACAGTAAC					60

AGTAGGGTCG AAA					73

( 2 ) INFORMATION FOR SEQ ID NO:7:

( i ) SEQUENCE CHARACTERISTICS:
        ( A ) LENGTH: 84 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:7:

CTGTAGAGAG GCAAGAAGTA CATGGAGGAG AAGTACCAGC TCAAGAAGGG AGCTGCTGGA					60

CGAGGCAGTG GAGTGGATCG TAGG					84

( 2 ) INFORMATION FOR SEQ ID NO:8:

( i ) SEQUENCE CHARACTERISTICS:
        ( A ) LENGTH: 84 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:8:

CTACCCTGCC GCACAACCTG ACAGAGGTCG CGCGCCCTCG GCGGTGCTCA CCAGGCCTGC					60

CTCTCCGCCG CACCTGCCAC CGAG					84

( 2 ) INFORMATION FOR SEQ ID NO:9:

( i ) SEQUENCE CHARACTERISTICS:
        ( A ) LENGTH: 76 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:9:

| | | | | | |
|---|---|---|---|---|---|
| AAAGCTAAGA | AGGATGACAG | AGTGCTAAGA | GGAGAAGTTA | GTACCTTGTC | TAGTAGTATC | 60
| TCGTTGCTAG | GCAAAG | | | | 76

( 2 ) INFORMATION FOR SEQ ID NO:10:

( i ) SEQUENCE CHARACTERISTICS:
        ( A ) LENGTH: 213 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:10:

| | | | | | |
|---|---|---|---|---|---|
| GGAGACTGTG | GCTTTGAGCA | TCCGTCAGAA | GTCCAGCATG | AGTGCATCCC | TCAGGCCATT | 60
| CTGGGAATGA | TGTCTGTGCC | AGGCCAAGTC | GGGCATGGGA | AAGACAGCAG | TGTTTGTCTT | 120
| GGCCACACTG | CAACAGCTGG | AGCCAGTTAC | TGGCAGGTGT | CTGTGCTGGT | GATGTGTACA | 180
| CTCGGAGTTG | GCTTTCAGAT | CAGCAGATAT | GAG | | | 213

( 2 ) INFORMATION FOR SEQ ID NO:11:

( i ) SEQUENCE CHARACTERISTICS:
        ( A ) LENGTH: 74 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:11:

| | | | | | |
|---|---|---|---|---|---|
| GCTAGGGAGT | AACCGAGATT | CGCTAAGAGG | AGAAGTTAGC | TACTTTGCTA | GTAGTATCCT | 60
| TCTGCGCTAG | AAAG | | | | | 74

( 2 ) INFORMATION FOR SEQ ID NO:12:

( i ) SEQUENCE CHARACTERISTICS:
        ( A ) LENGTH: 67 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:12:

| | | | | | |
|---|---|---|---|---|---|
| CTGTTTGAAC | GTATGATTCT | TGAGTTCTTG | AGATGGTTGT | ACTTTACCTT | TGAAGGTAAT | 60
| CTACCTG | | | | | | 67

( 2 ) INFORMATION FOR SEQ ID NO:13:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

| | |
|---|---|
| GCAAAGCAGG AGAAACCAC | 19

( 2 ) INFORMATION FOR SEQ ID NO:14:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:14:

GGGTCCATCT GATAGATATG AGAG                                              2 4

( 2 ) INFORMATION FOR SEQ ID NO:15:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: Nucleic Acid ( i x ) FEATURE:
    ( A ) NAME/KEY: misc_feature
    ( B ) LOCATION: 1..48
    ( D ) OTHER INFORMATION: /label=N
        / note= "N=I=Inosine"

( x i ) SEQUENCE DESCRIPTION: SEQ ID NO:15:

CUACUACUAC UAGGCCACGC GTCGACTACT ACGGGNNGGG NNGGGNNG                    4 8

IDENTIFICATION AND USE OF ANTIVIRAL COMPOUNDS THAT INHIBIT INTERACTION OF HOST CELL PROTEINS AND VIRAL PROTEINS REQUIRED FOR VIRAL REPLICATION

1. INTRODUCTION

The present invention relates to the identification of new cellular targets for viral intervention, the identification of antiviral compounds that act on the new targets, and the therapeutic use of such antiviral compounds.

2. BACKGROUND OF THE INVENTION

Influenza A virus is a negative strand RNA virus belonging to the orthomyxovirus family. The genome of the virus consists of 8 segments and encodes 10 polypeptides. Experimental evidence generated in the laboratory of Scholtissek indicates that the nucleoprotein (NP) is a major determinant of species specificity of influenza viruses (Scholtissek, et al., 1985, Virology 147: 287–294). Phylogenetic analysis divides NP genes into two families: one containing NPs predominantly of avian origin, and one containing those of human origin (Bean, 1984, Virology 133:438–442; Buckler-White & Murphy, 1986, Virology 155: 345–355; Gammelin, et al., 1989, Virology 170:71–80; Scholtissek, et al., 1985, supra). The human virus A/HK/1/68 and viruses having genetically related NPs cannot rescue mutants of the avian virus A/FPV/Rostock/1/34 with ts defects in the NP following double infection of chicken embryo fibroblasts (CEF) at 40° C. (Scholtissek, et al., 1985, supra; Scholtissek, et al., 1978, Virology 91: 79–85). However, the human viruses which failed to rescue the ts mutants on CEF cells were able to do so on Madin-Darby canine kidney(MDCK) cells (Scholtissek, et al., 1978, supra). Additionally, A/HK/1/68 virus and A/FPV/Rostock/1/34 virus reassortants containing the A/HK/1/68 virus-derived NP replicate in MDBK cells but not in CEFs (Scholtissek, et al., 1978, supra). The host-specific rescue of FPV ts mutants and the host restriction of A/HK/1/68 virus reassortants suggest that a factor(s) of host origin, which differs between mammalian and avian cells, is responsible for this phenomenon, and that this factor may interact with the influenza A virus NP.

Replication and transcription of influenza virus RNA requires four virus encoded proteins: the NP and the three components of the viral RNA-dependent RNA polymerase, PB1, PB2 and PA (Huang, et al., 1990, J. Virol. 64: 5669–5673). The NP is the major structural component of the virion which interacts with genomic RNA, and is required for antitermination during RNA synthesis (Beaton & Krug, 1986, Proc. Natl. Acad. Sci. USA 83:6282–6286). NP is also required for elongation of RNA chains (Shapiro & Krug, 1988, J. Virol. 62: 2285–2290) but not for initiation (Honda, et al., 1988, J. Biochem. 104: 1021–1026).

Little is known about host cell functions which contribute to the intracellular replication of influenza viruses, and cellular factors have not been characterized which directly interact with the viral proteins, much less cellular factor/viral interactions that can be used as targets for therapeutic intervention.

3. SUMMARY OF THE INVENTION

The present invention relates to the identification of host cell proteins that interact with viral proteins required for virus replication, and high throughput assays to identify compounds that interfere with the specific interaction between the viral and host cell protein. Interfering compounds that inhibit viral replication can be used therapeutically to treat viral infection.

The invention is based, in part, on the Applicants' discovery of a novel interaction between the NP of influenza virus and a human host cell protein. The host cell protein, referred to herein as NPI-1, may be an accessory protein required for replication of influenza virus. Compounds that interfere with the binding of the host cell and viral proteins, and inhibit viral replication can be useful for treating viral infection in vivo.

4. DESCRIPTION OF THE FIGURES

FIG. 1A and 1B: The interactive trap system. FIG. 1A: R100 contains the reporter gene LexAop-LEU2 and a transcriptionally inactive LexA-NP fusion protein (left). Library proteins are synthesized in R100 transformants in media containing galactose. If the library protein does not interact with the LexA-NP fusion protein, then the LEU2 gene is not transcribed (middle). If the library protein does interact with the LexA-NP fusion protein, then the LEU2 gene is transcriptionally active, and the cell forms a colony on $leu^-$ medium (right). FIG. 1B: The pLexA-NP bait plasmid used in the interactive trap. The coding region of influenza A/PR/8/34 virus nucleoprotein (NP) was subcloned into the EcoRI and Sal I restriction sites of pEG202. This construction encodes a fusion protein which includes 202 amino acids of LexA and the entire coding region of NP (498 amino acids) separated by 3 amino acids encoded by polylinker sequences derived from the cloning process.

FIG. 2A, 2B and 2C. Nucleotide sequence of NPI-1 cDNA (SEQ ID NO: 1) and deduced protein sequence (SEQ ID NO: 2). The coding sequence starts at nucleotide 1 and ends at nucleotide 1581. The 5' terminus of the library clone is indicated by an asterisk. Regions complementary to nested reverse transcription and 5'RACE primers are underlined.

FIG. 3. Comparison of NPI-1 (SEQ ID NO: 2) and SRP1 (SEQ ID NO: 3). Vertical lines indicate identity; colons and periods indicate conservative changes (Deveraux et al., 1984, Nucl. Acids Res. 12: 387–395). 42 amino acid ARM repeats are aligned vertically according to Peifer et al., 1994, Cell 76: 789–791. For a complete comparison of SRP1 to other ARM repeat containing proteins, see Peifer et al., 1994, supra. The ARM consensus sequence is indicated at the bottom; "+" indicates K,R, or H; "–" indicates D or E; "~" indicates a gap. Since other residues are conserved within the repeats of NPI-1 and SRP1, a consensus sequence derived from only these two proteins is also shown.

FIG. 4. GST-NPI-1 binds to NP in vitro. GST (lanes 1,5,6) and GST-NPI-1 (lanes 2,3,7,8) were expressed in bacteria and precipitated from cell lysates on glutathione agarose beads. The complexed beads were then incubated with partially purified influenza virus NP and polymerase preparations (Pol/NP) as indicated. Precipitated proteins were fractionated on a 12.5% SDS polyacrylamide gel, and either stained with Coomassie blue (lanes 1 to 3), or immunoblotted using the monoclonal antibody HT103 directed against the viral nucleoprotein (lanes 4 to 8). Unprecipitated Pol/NP was separated in lane 4. M, protein molecular weight markers; *, GST-NPI-1 fusion protein; arrows indicate major fusion protein degradation products.

FIG. 5. Immunoblot of total cellular proteins using polyclonal rabbit sera against NPI-1. Total cell lysates and cytoplasmic cell extracts from HeLa and MDBK cell lines were separated by SDS-PAGE, transferred to nitrocellulose, immunoblotted with anti-NPI-1 sera, and developed by $^{125}$I-protein A. Each lane contains protein from 1×105 cells.

Figure 6:
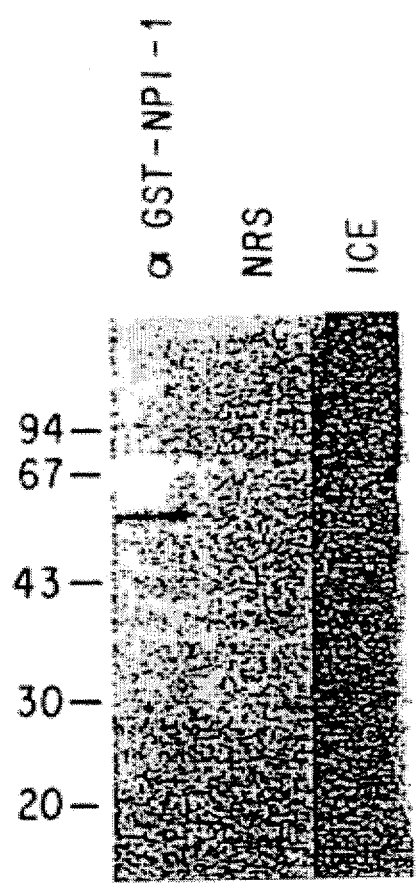

FIG. 6. NP is co-immunoprecipitated from influenza A virus infected cells by antisera against NPI-1. Infected HeLa cell proteins were labeled with $^{35}$S-methionine and $^{35}$S-cysteine, and total cell lysates were made as described in the text. Complexes of NPI-1 and NP were precipitated using anti-NPI-1 sera. Precipitated proteins were then fractionated by SDS-PAGE and detected by autoradiography.

FIGS. 7–15. Partial DNA sequences of isolated coding regions of nine different proteins that interact with the NP of influenza A, as detected using the interactive trap system in yeast. The proteins whose sequences are provided are as follows:

FIG. 7: HB3 (SEQ ID NO: 4)
FIG. 8: HB16 (SEQ ID NO: 5)
FIG. 9: HB39 (SEQ ID NO: 6)
FIG. 10: HB41 (SEQ ID NO: 7)
FIG. 11: HB56 (SEQ ID NO: 8)
FIG. 12: HB58 (SEQ ID NO: 9)
FIG. 13: HB60 (SEQ ID NO: 10)
FIG. 14: HB81 (SEQ ID NO: 11)
FIG. 15: HB94 (SEQ ID NO: 12)

5. DETAILED DESCRIPTION OF THE INVENTION

The present invention relates to the identification of host cellular proteins that interact with viral proteins important to viral replication and infection; the identification of compounds that interfere with the specific interaction of the host cell and viral proteins; and the evaluation and use of such compounds as antivirals in the treatment of viral infections in animals, including humans.

The invention is described in this section and in the example below for the identification and inhibition of interactions between human host cell proteins and influenza viral polymerase proteins. For clarity of discussion, particular detail is provided for the isolation of nucleoprotein interactor 1 (NPI-1), a human cell protein that interacts with the influenza virus NP protein. Since the interaction between NP and NPI-1 has never before been identified, it provides a novel target for antiviral treatment and serves as an excellent model for detailing the aspects of the invention. However, the principles may be analogously applied to the identification of other host cell proteins that interact with any of the four influenza virus proteins (PA, PB1, PB2, in addition to NP) required for viral RNA replication. The results of such further applications are indicated below.

The present invention also contemplates identifying interactions between host cell proteins and other viral proteins required for infection, such as, in the case of influenza virus, HA, NA, $M_1$, $M_2$, $NS_1$, and $NS_2$ proteins. The principles may also be analogously applied to other viruses, including but not limited to paramyxoviruses, such as parainfluenza viruses, measles viruses, respiratory syncytial virus, bunyviruses, arena viruses, the orthomyxo-like insect virus called Dhori, etc. The host cell proteins so identified may include completely novel proteins, or previously described proteins that have not yet been shown to interact with viral proteins.

Any method suitable for detecting protein-protein interactions may be employed for identifying novel viral-host protein interactions, and are considered within the scope of the present invention. For example, some traditional methods are co-immunoprecipitation, crosslinking and copurification through gradients or chromatographic columns. Newer methods result in the simultaneous identification of the genes coding for the protein interacting with a target protein. These methods include probing expression libraries with labeled target protein, using this protein in a manner similar to antibody probing of λgt11 libraries. One such method which detects protein interactions in vivo, the yeast interactive trap system, was successfully used to identify NPI-1 and nine other host cell protein sequences described herein, and is described in detail for illustration only and not by way of limitation.

The host cell/viral protein interactions identified are considered targets for antiviral intervention. Assays, such as the ones described herein can be used to identify compounds that interfere with such interactions. The compounds so identified which inhibit virus infection, replication, assembly, or release can be used as antivirals. In accordance with the invention, a given compound found to inhibit one virus may be tested for antiviral activity against a wide range of different viruses that have analogous dependencies on host cell proteins, including but not limited to paramyxoviruses, such as parainfluenza viruses, measles viruses, respiratory syncytial virus, bunyviruses, arena viruses, the orthomyxo-like insect virus called Dhori, etc.

The various aspects of the invention are described in the subsections below with specific reference to NPI-1, however, the invention is not limited to NPI-1 and encompasses any viral/host cell protein interactions as targets for therapeutic intervention.

5.1. IDENTIFICATION OF HOST CELL PROTEINS THAT INTERACT WITH VIRAL PROTEINS REQUIRED FOR REPLICATION

The previously unidentified gene for the host cell protein NPI-1 was cloned based on its ability to interact with the influenza A virus NP. The NPI-1 is the human homolog of the yeast protein SRP1. Interaction of NPI-1 and NP was demonstrated in yeast by the interactive trap system; in vitro coprecipitation of the NP with a bacterially expressed NPI-1 protein; and in infected cell extracts by coprecipitation of the NP with NPI-1, using anti-NPI-1 sera. The demonstration of this previously unknown interaction is illustrated in the working examples (see Section 6, infra). The data generated indicate that NPI-1 plays a role in the replication of influenza A viruses. NPI-1 is the first cellular protein characterized which interacts with a protein encoded by influenza viruses. This role, therefore, makes the inhibition of the NP-NPI-1 interaction an excellent target for antiviral therapy. It has not yet been demonstrated at what stage in the replication cycle NPI-1 functions. The NPI-1 could affect any of a number of NP functions which may include: (1) movement of the ribonucleoprotein complex (RNP) to the nucleus during viral entry; (2) vRNA synthesis, including antitermination and elongation; (3) mRNA synthesis, including elongation, polyadenylation, and transport to the cytoplasm; and (4) exit of the RNP from the nucleus during virion assembly.

The fact that both NPI-1 and SRP1 interact with proteins involved in RNA synthesis implies that there may be fundamental similarities between cellular DNA-dependent transcription and influenza viral RNA-dependent RNA synthesis. Cellular factors, like NPI-1, may be shared by the viral and the cellular RNA synthesis machinery to perform similar functions. In addition, the NPI-1 may tether the viral RNP to areas of the nuclear matrix where splicing and polyadenylation of mRNA occur. It should be noted that although NPI-1 was isolated from HeLa cells, this cell line is not productively infected by influenza A virus. However, HeLa cells synthesize influenza viral RNAs and proteins (see FIG. 6, lane 3), and have previously been used to examine viral RNA synthesis (Beaton & Krug, 1986, supra).

Figure 4:
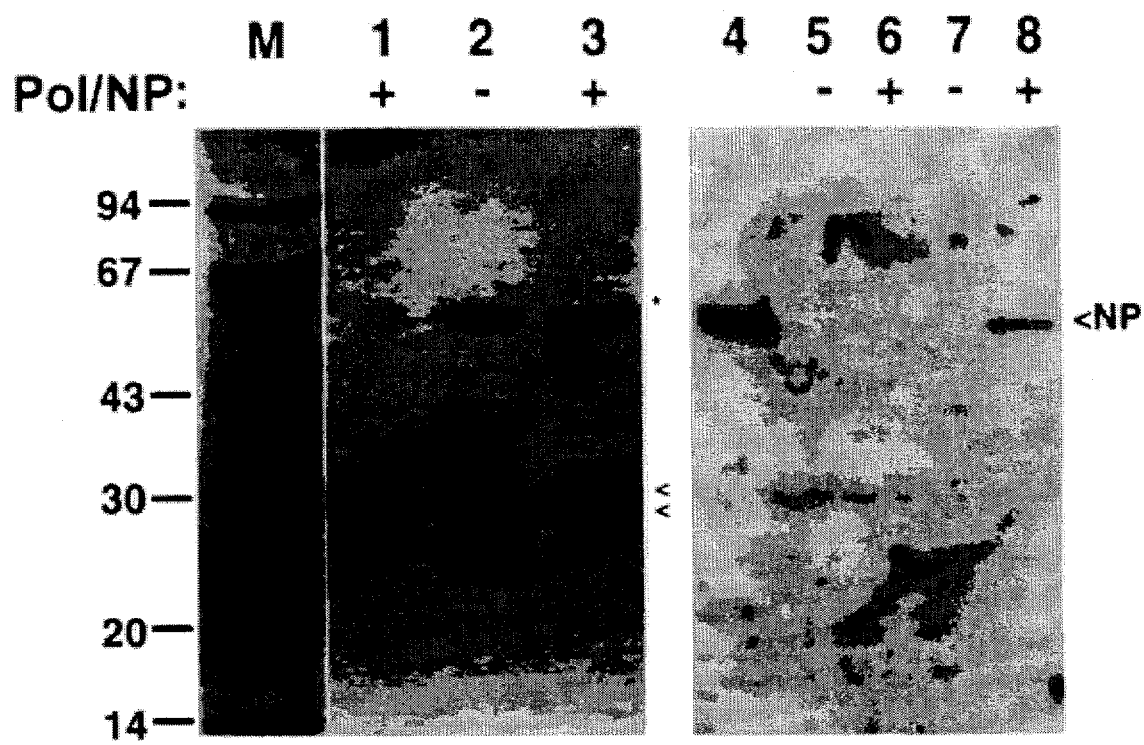
Figure 5:
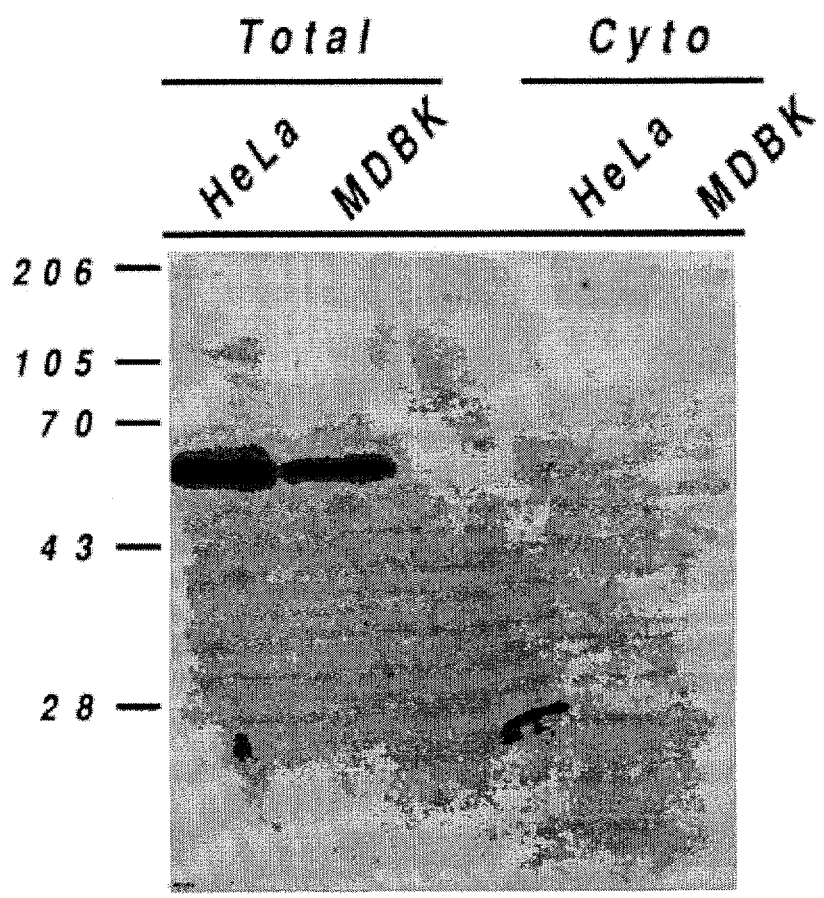

The viral NP exists in two forms in the infected cell. One form is associated with ribonucleoprotein complexes (RNP), and the other is a free form (Shapiro & Krug, 1988, supra). Pol/NP preparations used in coprecipitation experiments with NPI-1 were purified over cesium chloride/glycerol gradients (Honda et al., 1988, supra), which dissociate and purify virion proteins away from vRNA. The NP but not the polymerase proteins were detected on Coomassie stained gels in this experiment (FIG. 4, lane 3); however, coprecipitation of the viral polymerase proteins was not rigorously tested by immunoblot experiments. Only the NP was coprecipitated from infected HeLa cell extracts (FIG. 6) suggesting that it is free NP which is bound by NPI-1.

Only one host factor has been assigned a definitive function in the replication process of a negative strand RNA virus. The cellular casein kinase II has been shown to phosphorylate the phosphoprotein P of the vesicular stomatitis virus (VSV) RNA-dependent RNA polymerase. This is a step which appears to be required in order to activate the viral polymerase (Barik and Banerjee, 1992, Proc. Natl. Acad. Sci. USA 89: 6570–6574; Barik and Banerjee, 1992, J. Virol. 66: 1109–1118).

NPI-1 and SRP1 are 50% identical and 81% conserved at the amino acid level. This is a very high degree of conservation between proteins belonging to organisms as distantly related as humans and yeast, and suggests that the NPI-1/SRP1 performs a very basic function in the cell. NPI-1 and SRP1 have eight internal repeats, each of approximately 42-amino acids (FIG. 3 SEQ ID NO. 223). This repeat, termed the ARM motif, was originally identified in the Drosophila segment polarity gene armadillo (Riggleman, et al., 1989, Genes Dev. 3: 96–113), and it has been identified in a number of other proteins including β-catenin, plakoglobin, p120, APC and smGDS (Peifer et al., 1994, supra, and references therein). Several ARM proteins are associated with cell adhesion structures. Armadillo and its homologues bind to the C-terminal cytoplasmic tail of cadherins, a calcium-dependent class of cell adhesion molecules(CAMs), linking the CAMs to the underlying cytoskeleton at cell-cell junctions (McCrea, et al., 1991, Science 254: 1359–1361). In contrast to the armadillo protein, SRP1 and NPI-1 appear to be localized to the nucleus. If NPI-1, like SRP1 (Yano, et al., 1992, Mol. Cell. Biol. 12: 5640–5651), is associated with the nuclear membrane, it is possible that NPI-1 functions to tether viral RNP to the nuclear membranes (Jackson, et al., 1982, Nature 296: 366–368). It should be noted that NPI-1 may be related to (or identical with) a nuclear protein that has been found to be involved in V(D)J recombination (Cuomo et al., 1994, Meeting abstract F015, Keystone Symposium on Recombination).

The carboxyl terminal 265 amino acids of the NPI-1, which were sufficient for interaction with the viral NP, contain four and one-half ARM repeats. Individual repeats, in general, are approximately 30% identical with the ARM consensus sequence. This is consistent with the degree of conservation in ARM repeats of other proteins (Peifer et al., 1994, supra).

Using the same interactive trap system in yeast, nine additional DNA sequences were isolated which partially encode proteins that interact with the NP of influenza A virus. The various proteins so identified are listed in Table I.

TABLE I

INTERACTING HOST CELL PROTEINS

| Host Cell Proteins | FIG. | Comments |
| --- | --- | --- |
| NPI-1 | FIG. 2 | New protein sequence, homologous to SRP1 of Yeast |
| HB3 | FIG. 7 | New protein sequence |
| HB16 | FIG. 8 | Identical to sequences of hnRNP C proteins (Lahiri & Thomas, 1986, Nucl. Acids Res. 14: 4077–4094) |
| HB39 | FIG. 9 | New protein sequence |
| HB41 | FIG. 10 | New protein sequence |
| HB56 | FIG. 11 | New protein sequence |
| HB58 | FIG. 12 | New protein sequence |
| HB60 | FIG. 13 | New protein sequence |
| HB81 | FIG. 14 | New protein sequence |
| HB94 | FIG. 15 | New protein sequence |

The coding sequence for HB16 is identical to sequences coding for the previously identified hnRNP C proteins (Lahiri & Thomas, 1986, supra). The other eight additional coding sequences have not been identified before.

The invention contemplates, in addition to the DNA sequences disclosed herein, 1) any DNA sequence that encodes the same amino acid sequence as encoded by the DNA sequences shown in FIGS. 2 and 7–15; 2) any DNA sequence that hybridizes to the complement of the coding sequences disclosed herein (see FIGS. 2 and 7–15) under highly stringent conditions, e.g., washing in 0.1×SSC/0.1% SDS at 68° C. (Ausubel F.M. et al., eds., 1989, Current Protocols in Molecular Biology, Vol. I, Green Publishing Associates, Inc., and John Wiley & sons, Inc., New York, at p. 2.10.3) and encodes a functionally equivalent gene product; and/or 3) any DNA sequence that hybridizes to the complement of the coding sequences disclosed herein (see FIGS. 2 and 7–15) under less stringent conditions, such as moderately stringent conditions, e.g., washing in 0.2×SSC/0.1% SDS at 42° C. (Ausubel et al., 1989, supra), yet which still encodes a functionally equivalent gene product.

The invention also encompasses 1) DNA vectors that contain any of the coding sequences disclosed herein (see FIGS. 2 and 7–15), and/or their complements (i.e., antisense); 2) DNA expression vectors that contain any of the coding sequences disclosed herein (see FIGS. 2 and 7–15), and/or their complements (i.e., antisense), operatively associated with a regulatory element that directs the expression of the coding and/or antisense sequences; and 3) genetically engineered host cells that contain any of the coding sequences disclosed herein (see FIGS. 2 and 7–15), and/or their complements (i.e., antisense), operatively associated with a regulatory element that directs the expression of the coding and/or antisense sequences in the host cell. Regulatory element includes but is not limited to inducible and non-inducible promoters, enhancers, operators and other elements known to those skilled in the art that drive and regulate expression. The invention includes fragments of any of the DNA sequences disclosed herein.

Once the host cell proteins are obtained, they can be used to detect interactions with proteins from other viruses, in accordance with the invention. The following description is provided to illustrate this approach and not by way of limitation. Influenza B virus ribonucleoprotein complex was isolated and using a Western immunoblot assay, it was found that the cellular NPI-1 was associated with this complex. This result indicates that NPI-1, isolated based on its interaction with influenza A NP, also interacts with influenza B NP. Thus, compounds that inhibit influenza A NP-NPI-1 interactions and thereby inhibit influenza A infection should be similarly effective as antivirals against influenza B.

5.2. SCREENING ASSAYS FOR COMPOUNDS THAT INTERFERE WITH THE INTERACTION OF HOST CELL AND VIRAL PROTEINS REQUIRED FOR VIRAL REPLICATION

The host cell protein and the viral protein which interact and bind are sometimes referred to herein as "binding partners". This term also includes peptide fragments, produced as described in the subsections below, comprising the binding domain of each respective protein. Any of a number of assay systems may be utilized to test compounds for their ability to interfere with the interaction of the binding partners. However, rapid high throughput assays for screening large numbers of compounds, including but not limited to ligands (natural or synthetic), peptides, or small organic molecules are preferred. Compounds that are so identified to interfere with the interaction of the binding partners should be further evaluated for antiviral activity in cell based assays, animal model systems and in patients as described herein.

The basic principle of the assay systems used to identify compounds that interfere with the interaction between the viral and host cell proteins involves preparing a reaction mixture containing the viral protein and the host cell protein under conditions and for a time sufficient to allow the two proteins to interact and bind, thus forming a complex. In order to test a compound for inhibitory activity, the reaction is conducted in the presence and absence of the test compound, i.e., the test compound may be initially included in the reaction mixture, or added at a time subsequent to the addition of the viral and host cell protein; controls are incubated without the test compound or with a placebo. The formation of any complexes between the viral protein and the host cell protein is then detected. The formation of a complex in the control reaction, but not in the reaction mixture containing the test compound indicates that the compound interferes with the interaction of the viral protein and host cell protein.

The assay components and various formats that may be utilized are described in the subsections below.

5.2.1. ASSAY COMPONENTS

The host cell protein and viral protein binding partners used as components in the assay may be derived from natural sources, e.g., purified from cells and virus, respectively, using protein separation techniques well known in the art; produced by recombinant DNA technology using techniques known in the art (see e.g., Sambrook et al., 1989, Molecular Cloning: A Laboratory Manual, Cold Spring Harbor Laboratories Press, Cold Spring Harbor, N.Y.); and/or chemically synthesized in whole or in part using techniques known in the art; e.g., peptides can be synthesized by solid phase techniques, cleaved from the resin and purified by preparative high performance liquid chromatography (see, e.g., Creighton, 1983, Proteins: Structures and Molecular Principles, W. H. Freeman & Co., N.Y., pp. 50–60). The composition of the synthetic peptides may be confirmed by amino acid analysis or sequencing; e.g., using the Edman degradation procedure (see e.g., Creighton, 1983, supra at pp. 34–49).

The peptide fragments should be produced to correspond to the binding domains of the respective proteins. Any number of methods routinely practiced in the art can be used to identify and isolate the protein's binding site. These methods include but are not limited to mutagenesis of one of the genes encoding the protein and screening for disruption of binding in a co-immunoprecipitation assay, or mutagenesis of the host cell gene and selecting for resistance to viral infection. Compensating mutations in the viral gene can be selected which allow for viral growth in this mutant host. Sequence analysis of the genes encoding the respective proteins will reveal the mutations that correspond to the region of the protein involved in interactive binding. Alternatively, one protein can be anchored to a solid surface using methods described in section 5.2.2. infra, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene for the protein is obtained, short gene segments can be engineered to express peptide fragments of the protein, which can then be tested for binding activity and purified or synthesized.

Whether produced by molecular cloning methods or by chemical synthetic methods, the amino acid sequence of the binding partners which may be used in the assays of the invention need not be identical to the reported sequence of the genes encoding them. The binding partners may comprise altered sequences in which amino acid residues are deleted, added, or substituted resulting in a functionally equivalent product.

For example, functionally equivalent amino acid residues may be substituted for residues within the sequence resulting in a change of sequence. Such substitutes may be selected from other members of the class to which the amino acid belongs; e.g., the nonpolar (hydrophobic) amino acids include alanine, leucine, isoleucine, valine, proline, phenylalanine, tryptophan, and methionine; the polar neutral amino acids include glycine, serine, threonine, cysteine, tyrosine, asparagine, and glutamine; the positively charged (basic) amino acids include arginine, lysine, and histidine; the negatively charged (acidic) amino acids include aspartic and glutamic acid.

One of the binding partners used in the assay system should be labeled, either directly or indirectly, to facilitate detection of a complex formed between the viral and host cell proteins. Any of a variety of suitable labeling systems may be used including but not limited to radioisotopes such as $^{125}I$; enzyme labelling systems that generate a detectable colorimetric signal or light when exposed to substrate; and fluorescent labels.

Where recombinant DNA technology is used to produce the viral and host cell binding partners of the assay it may be advantageous to engineer fusion proteins that can facilitate labeling, immobilization and/or detection. For example, the coding sequence of the viral or host cell protein can be fused to that of a heterologous protein that has enzyme activity or serves as an enzyme substrate in order to facilitate labeling and detection. The fusion constructs should be designed so that the heterologous component of the fusion product does not interfere with binding of the host cell and viral protein.

Indirect labeling involves the use of a third protein, such as a labeled antibody, which specifically binds to one of the binding partners, i.e., either the host cell protein or viral protein used. Such antibodies include but are not limited to polyclonal, monoclonal, chimeric, single chain, Fab fragments and fragments produced by an Fab expression library.

For the production of antibodies, various host animals may be immunized by injection with the host cell protein or the viral protein, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72, Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce single chain antibodies specific to one of the binding partners.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

5.2.2. ASSAY FORMATS

The assay can be conducted in a heterogeneous or homogeneous format. Heterogeneous assays involve anchoring one of the binding partners onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the binding partners, e.g., by competition, can be identified by conducting the reaction in the presence of the test substance; i.e., by adding the test substance to the reaction mixture prior to or simultaneously with the viral protein and host cell protein. On the other hand, test compounds that disrupt preformed complexes, e.g. compounds with higher binding constants that displace one of the binding partners from the complex, can be tested by adding the test compound to the reaction mixture after complexes have been formed. The various formats are described briefly below.

In a heterogeneous assay system, one binding partner, e.g., either the viral protein or the host cell protein, is anchored onto a solid surface, and its binding partner, which is not anchored, is labeled, either directly or indirectly. In practice, microtiter plates are conveniently utilized. The anchored species may be immobilized by non-covalent or covalent attachments. Non-covalent attachment may be accomplished simply by coating the solid surface with a solution of the protein and drying. Alternatively, an immobilized antibody specific for the protein may be used to anchor the protein to the solid surface. The surfaces may be prepared in advance and stored.

In order to conduct the assay, the binding partner of the immobilized species is added to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the binding partner was pre-labeled, the detection of label immobilized on the surface indicates that complexes were formed. Where the binding partner is not pre-labeled, an indirect label can be used to detect complexes anchored on the surface; e.g., using a labeled antibody specific for the binding partner (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one binding partner to anchor any complexes formed in solution, and a labeled antibody specific for the other binding partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the host cell and viral protein is prepared in which one of the binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the binding partners from the preformed complex will result in the generation of a signal above background. In this way, test substances which disrupt the viral protein-host cell protein interaction can be identified.

For example, in a particular embodiment for NPI-1, NPI-1 can be prepared for immobilization using recombinant DNA techniques described in section 5.2.1., supra. Its coding region can be fused to the glutathione-S-transferase (GST) gene using the fusion vector pGEX-5X-1, in such a manner that its binding activity is maintained in the resulting fusion protein. NP can be purified and used to raise a monoclonal antibody, specific for NP, using methods routinely practiced in the art and described above. This antibody can be labeled with the radioactive isotope $^{125}$I, for example, by methods routinely practiced in the art. In a heterogeneous assay, e.g., the GST-NPI-1 fusion protein can be anchored to glutathione-agarose beads. NP can then be added in the presence or absence of the test compound in a manner that allows NP to interact with and bind to the NPI-1 portion of the fusion protein. After the test compound is added, unbound material can be washed away, and the NP-specific labeled monoclonal antibody can be added to the system and allowed to bind to the complexed binding partners. The interaction between NP and NPI-1 can be detected by measuring the amount of radioactivity that remains associated with the glutathione-agarose beads. A successful inhibition of the interaction by the test compound will result in a decrease in measured radioactivity.

Alternatively, the GST-NPI-1 fusion protein and NP can be mixed together in liquid in the absence of the solid glutathione-agarose beads. The test compound can be added either during or after the binding partners are allowed to interact. This mixture can then be added to the glutathione-agarose beads and unbound material is washed away. Again the extent of inhibition of the binding partner interaction can be detected by measuring the radioactivity associated with the beads.

In another embodiment of the invention, these same techniques can be employed using peptide fragments that correspond to the binding domains of NP and NPI-1, respectively, in place of one or both of the full length proteins. These binding domains can be identified, as described in section 5.2.1., supra. For example, and not by way of limitation, NPI-1 can be anchored to a solid material as described above in this section by making a GST-NPI-1 fusion protein and allowing it to bind to glutathione agarose beads. NP can be labeled with a radioactive isotope, such as $^{35}$S, and cleaved with a proteolytic enzyme such as trypsin. Cleavage products can then be added to the anchored GST-NPI-1 fusion protein and allowed to bind. After washing away unbound peptides, labeled bound material, representing the NP binding domain, can be eluted, purified, and analyzed for amino acid sequence by methods described in section 5.2.1., supra. Peptides so identified can be produced synthetically or fused to appropriate facilitative proteins using recombinant DNA technology, as described in section 5.2.1., supra.

In accordance with the invention, a given compound found to inhibit one virus may be tested for general antiviral activity against a wide range of different viruses that have analogous dependencies on host cell proteins. For example, and not by way of limitation, a compound which inhibits the interaction of influenza virus NP with NPI-1 by binding to the NP binding site can be tested, according to the assays described in section 5.3. infra, against other viruses, particularly those which have similar proteins, e.g., parainfluenza viruses.

5.3. ASSAYS FOR ANTIVIRAL ACTIVITY

Any of the inhibitory compounds which are identified in the foregoing assay systems may be tested for antiviral activity.

5.3.1. VIRAL GROWTH ASSAYS

The ability of an inhibitor identified in the foregoing assay systems to prevent viral growth can be assayed by plaque formation or by other indices of viral growth, such as the $TCID_{50}$ or growth in the allantois of the chick embryo. In these assays, an appropriate cell line or embryonated eggs are infected with wild-type influenza virus, and the test compound is added to the tissue culture medium either at or after the time of infection. The effect of the test compound is scored by quantitation of viral particle formation as indicated by hemagglutinin (HA) titers measured in the supernatants of infected cells or in the allantoic fluids of infected embryonated eggs; by the presence of viral plaques; or, in cases where a plaque phenotype is not present, by an index such as the $TCID_{50}$ or growth in the allantois of the chick embryo, or with a hemagglutination assay.

An inhibitor can be scored by the ability of a test compound to depress the HA titer or plaque formation, or to reduce the cytopathic effect in virus-infected cells or the allantois of the chick embryo, or by its ability to reduce viral particle formation as measured in a hemagglutination assay.

5.3.2 ANIMAL MODEL ASSAYS

The ability of an inhibitor to prevent replication of influenza virus can be assayed in animal models that are natural or adapted hosts for influenza. Such animals may include mammals such as pigs, ferrets, mice, monkeys, horses, and primates, or birds. As described in detail in Section 5.5 infra, such animal models can be used to determine the $LD_{50}$ and the $ED_{50}$ in animal subjects, and such data can be used to derive the theraputic index for the inhibitor of the viral/host cell protein interaction.

5.4. INHIBITORY COMPOUNDS

Inhibitory compounds identified in the foregoing screening assays which may be used in accordance with the invention may include but are not limited to small organic molecules, peptides and antibodies.

For example, peptides having an amino acid sequence corresponding to the domain of the host cell protein that binds to the viral protein may be used to compete with the native viral protein and, therefore, may be useful as inhibitors in accordance with the invention. Similarly, peptides having an amino acid sequence corresponding to the domain of the viral protein that binds to the host cell protein may be used. Such peptides may be synthesized chemically or produced via recombinant DNA technology using methods well known in the art (e.g., see Creighton, 1983, supra; and Sambrook et al., 1989, supra). Lipofectin or liposomes may be used to deliver the peptides to cells.

Alternatively, antibodies that are both specific for the binding domains of either the host cell or viral proteins and interfere with their interaction may be used. Such antibodies may be generated using standard techniques described in Section 5.2.1., supra, against the proteins themselves or against peptides corresponding to the binding domains of the proteins. Such antibodies include but are not limited to polyclonal, monoclonal, Fab fragments, single chain antibodies, chimeric antibodies, etc. Where whole antibodies are used, internalizing antibodies are preferred. However, lipofectin may be used to deliver the antibody or a fragment of the Fab region which binds to the viral or host cell protein epitope into cells. Where fragments of the antibody are used, the smallest inhibitory fragment which binds to the target protein's binding domain is preferred.

5.5. PHARMACEUTICAL PREPARATIONS AND METHODS OF ADMINISTRATION

The identified compounds that inhibit viral replication can be administered to a patient at therapeutically effective doses to treat viral infection. A therapeutically effective dose refers to that amount of the compound sufficient to result in amelioration of symptoms of viral infection.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of infection in order to minimize damage to uninfected cells and reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal infection, or a half-maximal inhibition) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

6. EXAMPLE

THE IDENTIFICATION OF NPI-1 AND ITS INTERACTION WITH INFLUENZA NUCLEOPROTEIN

We used the yeast interactive trap system to identify a cellular protein which interacts with the nucleoprotein of influenza A viruses. This protein, nucleoprotein interactor 1 (NPI-1) is the human homologue of the yeast protein SRP1. SRP1 was previously identified as a suppressor of temperature-sensitive RNA polymerase I mutations (Yano, et. al., 1992, Mol. Cell. Biol. 12:5640–5651). A full length CDNA clone of NPI-1 was generated from HeLa cell poly A+RNA. The viral NP, which had been partially purified from influenza A/PR/8/34 virus-infected embryonated eggs, could be coprecipitated from solution by glutathione agarose beads complexed with a bacterially expressed glutathione-S-transferase (GST)-NPI-1 fusion protein, confirming the results of the yeast genetic system. Antisera raised against NPI-1 identified a 65 kDa polypeptide from total cellular extracts of both HeLa and MDBK cells. In addition, the viral nucleoprotein was co- immunoprecipitated from influenza A/WSN/33 virus-infected HeLa cells by antisera directed against NPI-1, demonstrating an interaction of these two proteins in infected cells, and suggesting that NPI-1 plays a role during influenza virus replication.

6.1. MATERIALS AND METHODS

6.1.1. YEAST, BACTERIA AND PLASMIDS

Yeast strain EGY48 (Mata trpl ura3 his3 LEU2::pLEXAop6-LEU2) (Zervos et al., 1993, Cell 72: 222–232) and plasmids pEG202, pSH18–34, and pRFHM1 and the HeLa cell cDNA library constructed in pJG4–5 (Gyuris et al., 1993, Cell 75: 791–803) were previously described. Similar versions of these plasmids and this yeast host strain are available commercially from Clontech as part of a two fusion protein system. pLexA-NP was constructed by subcloning the cDNA of influenza A/PR/8/34 NP as a LexA translational fusion gene into pEG202 (FIG. 1). Yeast strains constructed as part of these studies are described in Table 2. Escherichia coli MH3 (trpC araD lacX hsdR galU galK) and W31005 were previously described (Hall et al., 1984, Cell 36: 1057–1065).

6.1.2. SELECTION OF NP INTERACTORS

An interactive trap selection was performed essentially as has been previously described (Gyuris, et al., 1993, supra; Zervos, et al., 1993, supra). Strain R100 was transformed by the HeLa cDNA library using the lithium acetate method (Ito, et al., 1983, J. Bacteriol. 153: 163–168). $2 \times 10^6$ primary yeast transformants were selected on twelve 25×25 cm² his trp⁻-glucose plates, pooled and stored at –70° C. Library transformants were selected for leu+ phenotype on his leu-galactose plates; the efficiency of plating was approximately $10^{-4}$ leu+ colonies per galactose+ colony. Plasmid DNA was isolated from leu+ library transformants as described by Hoffman and Winston (Hoffman & Winston, 1987, Gene 57: 267–272) and introduced into MH3 cells by electroporation. Library plasmids were selected by plating the transformation mix on 1×A+amp+glucose plates (Miller, 1972, Experiments in Molecular Genetics, Cold Spring Harbor Laboratory Press, Cold Spring Harbor, N.Y.).

cDNAs were analyzed by checking the specificity of interaction with the NP. Each isolated plasmid was introduced into strains R101 and R102. These strains harbor pSH18–34, a reporter plasmid encoding β-galactosidase with a GAL1 promoter transcriptionally controlled from upstream LexA binding sites. Strain R102 was used as a negative control for NP-specificity of cloned cDNAs. It contains pRFHM1, which encodes LexA fused to a transcriptionally inert fragment of the Drosophila melanogaster bicoid protein. β-Galactosidase activity was assayed on nitrocellulose replicas of the colonies by freeze fracturing the cells and incubating in buffer containing 5-bromo-4-chloro-3-indolyl-β-D-galactoside (X-gal) (Miller, 1972, supra). Plasmids which conferred both a leu+ and β-gal+ phenotypes in the presence of pLexA-NP but not in the presence of pRFHM1 were saved for further study.

6.1.3. CLONING OF THE 5' TERMINUS OF NPI-1

The 5' terminus of NPI-1 was cloned by rapid amplification of cDNA ends ("RACE") by the method of Frohman (Frohman, 1990, in PCR Protocols: A Guide to Methods and Applications, Innis et. al., eds., Academic Press Inc., San Diego, p. 28–38; Frohman, et al., 1988, Proc. Natl. Acad. Sci. USA 85: 8998–9002). Reverse transcription of 1 µg of poly A+ HeLa cell RNA was performed using the NPI-1 specific oligonucleotide 5'GCAAAGCAGGAGAAACCAC3'(SEQ ID NO: 13). First strand cDNA was tailed with dCTP by terminal transferase. PCR amplification of the reverse transcription product was performed with the nested NPI-1 primer 5'GGGTCCATCTGATAGATATGAGAG3'(SEQ ID NO: 14) and the 5' RACE anchor primer 5'CUACUACUACUAGGCCACGCGTCGACTACTAC-GGGIIGGGIIGGGIIG3'(SEQ ID NO: 15) (Gibco/BRL). The PCR product was subcloned into pGEM-T (Promega) and was sequenced by standard protocols. 5'RACE products from three independent experiments were cloned and sequenced in order to avoid errors introduced by PCR.

6.1.4. BACTERIAL EXPRESSION AND PURIFICATION OF GST-NPI-1

The NPI-1 CDNA derived from a HeLa CDNA library was subcloned between the EcoRI and XhoI restriction endonuclease sites of the glutathione-S-transferase fusion vector pGEX-5X-1 (Pharmacia) to generate the plasmid pGST-NPI-1. Protein was induced from bacterial expression plasmids in W31005 cells with isopropyl-β-D-galactopyranoside according to standard protocols (Smith & Johnson, 1988, Gene 67: 31–40). Bacteria were pelleted 4 h after induction, washed in ice cold phosphate buffered saline (PBS), and resuspended in one-tenth culture volume PBS+ 1% Triton X-100. Bacteria were lysed on ice with four 15 s pulses in a Raytheon sonicator at an output setting of 1 amp. Insoluble material was pelleted at 50,000×g for 30 min in a Beckman TL-100.3 rotor.

GST-NPI-1 and GST were purified from bacterial lysates on glutathione-agarose beads(Sigma Chemical Corp.). Beads were swelled according to the manufacturer's instructions and equilibrated in PBS. Typical binding reactions were done in 500 µl of PBS/0.1% Triton X-100, and included 50 µl bacterial lysate and 10 µl of a 50% slurry of glutathione-agarose beads. Binding reactions were incubated for 5 min at room temperature on a rotating wheel. Beads were collected by centrifugation for 5 s in a microfuge, and were washed three times in PBS.

6.1.5. NP BINDING ASSAY

To assay binding of NP to GST-NPI-1/bead complexes typical reactions were performed in 500 µl of ice cold PBS+0.05% Nonidet P-40 and contained washed GST-NP1-1/bead complexes and 10 µg partially purified influenza virus polymerase and nucleoprotein preparations (Pol/NP). Virus was prepared from embryonated eggs infected by influenza A/PR/8/34 virus and POL/NP preparations were purified as previously described (Enami, et al., 1990, Proc. Natl. Acad. Sci. USA 87: 3802–3805; Parvin, et al., 1989, J. Virol. 63: 5142–5152). NP was bound for 1 h at 4° C. on a rotating wheel. Beads were collected by centrifugation for 5 s in a microfuge, and were washed three times in PBS+ 0.05% NP-40. Washed beads were resuspended in 50 µl SDS sample buffer (Sambrook, et al., 1989, Molecular Cloning: A Laboratory Manual, Cold Spring Harbor Laboratories Press, Cold Spring Harbor, N.Y.), boiled for 5 min, and pelleted in a microfuge. 10 µl of each supernatant was separated by electrophoresis on a 12.5% SDS-polyacrylamide gel.ABgels were either stained with Coomassie blue or processed for immunoblot analysis. NP was detected by immunoblotting with the monoclonal antibody HT103.

6.1.6. ANTISERA AND IMMUNOBLOTTING

Polyclonal rabbit antisera against NPI-1 was generated by immunization of a female NZY Rabbit (Buckshire Farms) with 200 µg of purified GST-NPI-1 in complete Freund's adjuvant, followed by two boosts of 100 µg in incomplete Freund's adjuvant at three week intervals. The specificity of antisera was demonstrated by immunoblot analysis of GST-NPI-1 in bacterial lysates. Immunoblots were performed by standard methods (Harlow and Lane, 1998, Antibodies: A Laboratory Manual. Cold Spring Harbor Laboratories Press, Cold Spring Harbor, N.Y.). Sera were used at a dilution of 1:1000.

6.1.7. VIRUSES AND CELLS

Total cell lysates from HeLa and MDBK cells were generated by direct lysing of cells in SDS-sample buffer, followed by shearing of chromosomal DNA by passage through a 21 ga. syringe. Cytoplasmic extracts were generated by lysing cells in ice cold NP-40 lysis buffer (10 mM Tris-Cl, pH 8.0; 100 mM NaCl; 1 mM EDTA; 1 mM DTT; 1% Nonidet P-40; 1 mM 4-(2-aminoethyl) benzenesulfonylfluoride-hydrochloride (Pefabloc)). After 10 min on ice nuclei were removed by centrifugation. Proteins were separated by SDS-PAGE, transferred to nitrocellulose and visualized by immunoblotting.

To generate infected cell lysates containing metabolically labeled proteins $4 \times 10^6$ HeLa cells were infected with influenza A/WSN/33 virus at a multiplicity of 10 for 45 min at 37° C. Infection was allowed to proceed in DMEM+0.1% BSA for 5 h at which time cells were labeled with 50 ACi $^{35}$S-methionine+50 µCi $^{35}$S-cystine in MEM-cys-met for 1 h. Extracts were prepared by resuspending infected cells in 650 µl ice cold NP-40 lysis buffer followed by two 15 s pulses in a Raytheon sonicator to disrupt nuclei. Insoluble cell debris was removed by centrifugation at 100,000× g in a TL-100.3 Beckman rotor. 5 µl anti-NPI-1 sera was incubated on ice for 1 h with 100 µl infected cell lysates. Immune complexes were precipitated from solution by incubation with Sepharose-4B linked protein G beads (Sigma) for 1 h. Beads were collected by centrifugation, washed three times in NP-40 lysis buffer, and resuspended in SDS-sample buffer. Precipitated proteins were separated by SDS-PAGE and visualized by autoradiography.

6.2. RESULTS

6.2.1. ISOLATION OF NPI-1

The interactive trap was used to identify proteins which specifically interact with the influenza A virus nucleoprotein (NP). The interactive trap is one of several genetic systems recently developed which uses the modular nature of transcription activators to detect protein:protein interactions (Chien, et al., 1991, Proc. Natl. Acad. Sci. USA 88: 9578–9582; Dalton & Treisman, 1992, Cell 68: 597–612; Durfee, et al., 1993, Genes Dev. 7: 555–569; Gyuris, et al., 1993, supra; Vojtek, et al., 1993, Cell 74: 205–214; Zervos, et al., 1993, supra). The interactive trap consists of three components:

(1) a reporter gene that has no basal transcription;
(2) a fusion protein which contains a LexA DNA binding domain that is transcriptionally inert; and
(3) proteins encoded by an expression library, which are expressed as fusion proteins containing an activation domain (FIG. 1A). Interaction of the LexA fusion protein and the fusion protein containing the activation domain will constitute a bimolecular transcriptional activator which, in this case, will confer the ability to grow on media lacking leucine (Gyuris, et al., 1993, supra; Zervos, et al., 1993, supra). In the absence of this interaction the leu2 gene is not transcribed.

The NP gene of influenza A/PR/8/34 virus was subcloned as a translational fusion gene with the LexA gene into pEG202 to generate pLexA-NP (FIG. 1B). Strain R100 (Table II), which contains pLexA-NP, was transformed with a HeLa cell cDNA library constructed in pJG4-5. pJG4-5 contains an activation domain under control of a GAL1 promoter (Gyuris, et al., 1993, supra).

TABLE II

| YEAST STRAINS USED | |
|---|---|
| Strains | Genotype |
| EGY48 | Mata trp1 ura3 his3 LEU2::pLEXAop6-LEU2 |
| R100 | EGY48, pLexA-NP (TRP1) |
| R101 | EGY48, pLexA-NP, pSH18-34 (HIS3) |
| R102 | EGY48, pRFHM1 (TRP1), pSH18-34 |

Library plasmids were rescued from 100 leu+ colonies. Reproducibility of the interaction of the NP with the encoded library proteins was tested by transforming library plasmids into strain R101. Transformants were screened for galactose-dependent β-galactosidase activity and growth on media lacking leucine. Specificity for NP was analyzed by checking the ability of library plasmids to confer growth on leu⁻ media and β-galactosidase activity in connection with a different LexA fusion plasmid, pRFHM1, encoding a fragment of the *Drosophila melanogaster* bicoid protein. Twenty-three library plasmids were confirmed to encode NP-interactive proteins. Twelve identical 2.1 kbp clones encoded the carboxy terminal fragment of a protein termed nucleoprotein interactor 1 (NPI-1). Partial DNA sequencing showed that NPI-1 is the human homologue of the yeast SRP1 gene (infra).

6.2.2. CLONING AND SEQUENCING OF THE NPI-1 CDNA

The 2.1 kbp NPI-1 cDNA in pJG4-5 was sequenced by standard protocols. The 5° CDNA terminus of the NPI-1 gene was cloned by 5' RACE. cDNAs from 3 independently derived NPI-1 5'RACE products were cloned and sequenced. Nucleotide and derived amino acid sequences of NPI-1 are shown in FIG. 2. The sequence reveals a 2.9 kbp cDNA which encodes a protein of 527 amino acids with a calculated molecular weight of 58,754 Da and a pI=4.74. The carboxyl terminal 265 amino acids were encoded by the interactive trap library plasmid and interact with the viral NP.

Comparison of the deduced amino acid sequences in the GenBank and EMBL data bases using the FASTA and TFASTA programs (Deveraux, et al., 1984, Nucleic Acids Res. 12:387–395) demonstrated that NPI-1 is the human homologue of the *Saccharomyces cerevisiae* protein SRP1 (Yano, et al., 1992, Mol. and Cell. Biol. 12:5640–5651). SRP1 was cloned as an allele-specific suppressor of ts mutations in the zinc-binding domain of the A190 subunit of RNA polymerase I. The amino acid sequence is highly conserved between NPI-1 and SRP1:50% identity and 81% similarity at the amino acid level. The amino terminus of NPI-1 has a potential nuclear localization signal (Chelsky, et al., 1989, Mol. Cell. Biol. 9:2487–2492); amino acids 25 to 49 are rich in arginine, and contain a stretch of four consecutive arginines at amino acids 28 to 31. NPI-1, like SRP1, contains a series of 8 consecutive ARM motifs, which are 42 amino acid protein subsequences originally identified in the *Drosophila armadillo* protein (Peifer et al., Cell 76: 789–791, 1994; Yano, et al., 1992, supra) (FIG. 3, infra).

6.2.3. NPI-1 BINDS TO NP IN VITRO

In order to demonstrate that the NPI-1 binds to the viral NP, the NPI-1 CDNA fragment (amino acids 262 to 527)

was subcloned into the bacterial expression vector pGEX-5X-1 yielding a glutathione S-transferase fusion gene. The expressed fusion protein was purified from bacterial lysates on glutathione agarose beads. NP, which had been partially purified with the viral polymerase from influenza A/PR/8/34 virus was specifically precipitated from solution by glutathione agarose beads complexed with GST-NPI-1 (FIG. 4). The NP band migrates slightly faster than that of the GST-NPI-1 fusion protein. The identity of this protein was confirmed by immunoblot analysis using the anti-NP monoclonal antibody HT103 (FIG. 4, lane 8).

6.2.4. IMMUNODETECTION OF NPI-1 IN CELL EXTRACTS

Rabbit antisera raised against GST-NPI-1 were used to identify a polypeptide from total cellular extracts of both HeLa and MDBK cells with an apparent molecular weight of 65 kDa (FIG. 5). The molecular weight predicted from the derived amino acid sequence of the cDNA is slightly smaller (59 kDa). A lower amount of NPI-1 was present in the cytoplasmic fraction generated by lysis of cells in the presence of NP-40 than in the total cellular extract suggesting that most of NPI-1 is located in the nucleus (FIG. 5). This is consistent with results localizing the NPI-1 homologue SRP1 to the nucleus of yeast cells by immunofluorescence (Yano, et al., 1992, supra). We have been unable to localize NPI-1 to a particular intracellular compartment by immunofluorescence experiments using our antisera due to the high background fluorescence of these preparations.

6.2.5. NPI-1 INTERACTS WITH NP IN INFECTED CELLS

Since NP formed a complex with NPI-1 in vitro, we examined whether NP and NPI-1 form a complex in infected cells. NP was specifically coimmunoprecipitated from extracts of influenza A/WSN virus infected HeLa cells by antisera directed against NPI-1 (FIG. 6). This demonstrates an interaction of the viral NP and the cellular NPI-1 during influenza A virus infection.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An isolated nucleic acid molecule comprising a nucleotide sequence that (a) encodes a nucleoprotein interactor-1 protein having the amino acid sequence SEQ ID NO: 2; or (b) is the complement of the nucleotide sequence of (a).

2. An isolated nucleic acid molecule comprising a nucleotide sequence that hybridizes under moderately stringent conditions to the nucleic acid of claim 1 and encodes a naturally occurring nucleoprotein interactor-1 protein.

3. The nucleic acid molecule of claim 2 in which the encoded protein occurs naturally in a human cell.

4. An isolated nucleic acid molecule comprising a nucleotide sequence that hybridizes under moderately stringent conditions to the nucleic acid of claim 1 and encodes a naturally occurring protein that interacts with viral nucleoprotein.

5. The nucleic acid molecule of claim 4 in which the encoded protein occurs naturally in a human cell.

6. A nucleic acid molecule comprising a nucleotide sequence that (a) encodes the amino acid sequence of SEQ ID NO:2 in which at least one but not all of the following segments of amino acid residues is deleted: from amino acid residues 1-105, 106-150, 151-192, 193-235, 236-277, 278-318, 319-360, 361-402, 403-445, 446-527, 1-262, or 263-527; or (b) is the complement of the nucleotide sequence of (a).

7. A nucleic acid molecule comprising a fragment of the nucleotide sequence of SEQ. ID NO: 1 that (a) encodes a polypeptide having one or more of the following amino acid sequences of SEQ ID NO: 2: from amino acid residues 1-105, 106-150, 151-192, 193-235, 236-277, 278-318, 319-360, 361-402, 403-445, 446-527, 1-262, or 263-527; or (b) is the complement of the nucleotide sequence of (a).

8. A DNA vector containing the nucleotide sequence of claim 1, 2, 3, 4, 5, 6, or 7.

9. An expression vector containing the nucleotide sequence of claim 1, 2, 3, 4, 5, 6, or 7 operatively associated with a regulatory nucleotide sequence containing transcriptional and translational regulatory information that controls expression of the nucleotide sequence in a host cell.

10. A genetically engineered host cell containing the nucleotide sequence of claim 1, 2, 3, 4, 5, 6, or 7.

11. A genetically engineered host cell containing the nucleotide sequence of claim 1, 2, 3, 4, 5, 6, or 7 operatively associated with a regulatory nucleotide sequence containing transcriptional and translational regulatory information that controls expression of the nucleotide sequence in a host cell.

* * * * *

UNITED STATES PATENT AND TRADEMARK OFFICE
CERTIFICATE OF CORRECTION

PATENT NO.    : 5,750,394

DATED         : May 12, 1998

INVENTOR(S)   : Palese et al.

It is certified that error appears in the above-identified patent and that said Letters Patent is hereby corrected as shown below:

Column 1, before the Introduction, insert --This invention was made with government support under grant number 5 R01 AI11823-20 awarded by the National Institutes of Health. The government has certain rights in the invention.--

Signed and Sealed this

Twenty-first Day of March, 2000

Attest:

Q. TODD DICKINSON

Attesting Officer

Commissioner of Patents and Trademarks